US010584121B2

(12) United States Patent
Zhang et al.

(10) Patent No.: US 10,584,121 B2
(45) Date of Patent: Mar. 10, 2020

(54) HETEROARYL SUBSTITUTED BENZOIC ACIDS AS RORGAMMAT INHIBITORS AND USES THEREOF

(71) Applicant: Merck Sharp & Dohme Corp., Rahway, NJ (US)

(72) Inventors: Hongjun Zhang, Boston, MA (US); Kenneth Jay Barr, Boston, MA (US); Blair T. Lapointe, Brookline, MA (US); Hakan Gunaydin, Somerville, MA (US); Kun Liu, Needham, MA (US); B. Wesley Trotter, Medfield, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/770,257

(22) PCT Filed: Oct. 27, 2016

(86) PCT No.: PCT/US2016/059067
§ 371 (c)(1),
(2) Date: Apr. 23, 2018

(87) PCT Pub. No.: WO2017/075185
PCT Pub. Date: May 4, 2017

(65) Prior Publication Data
US 2019/0194186 A1 Jun. 27, 2019

Related U.S. Application Data

(60) Provisional application No. 62/246,915, filed on Oct. 27, 2015.

(51) Int. Cl.
| | | |
|---|---|---|
| C07D 471/04 | (2006.01) | |
| A61K 31/4353 | (2006.01) | |
| A61P 37/00 | (2006.01) | |
| A61P 11/06 | (2006.01) | |
| A61P 19/02 | (2006.01) | |
| A61P 29/00 | (2006.01) | |

(52) U.S. Cl.
CPC ............ *C07D 471/04* (2013.01); *A61P 11/06* (2018.01); *A61P 19/02* (2018.01); *A61P 29/00* (2018.01); *A61P 37/00* (2018.01)

(58) Field of Classification Search
CPC ................................ C07D 471/04; A61P 37/00
USPC ......................................................... 514/303
See application file for complete search history.

(56) References Cited

U.S. PATENT DOCUMENTS

| | | | |
|---|---|---|---|
| 4,670,447 A | 6/1987 | Strupczewski | |
| 4,751,235 A | 6/1988 | Anderson | |
| 5,583,152 A | 12/1996 | Bernstein et al. | |
| 5,639,780 A | 6/1997 | Lau et al. | |
| 5,985,903 A | 11/1999 | Assmann et al. | |
| 6,020,354 A | 2/2000 | Assmann et al. | |
| 6,037,367 A | 3/2000 | Christensen, IV et al. | |
| 6,133,290 A | 10/2000 | Krushinski, Jr. et al. | |
| 6,160,001 A | 12/2000 | Assmann et al. | |
| 6,172,092 B1 | 1/2001 | Assmann et al. | |
| 6,180,643 B1 | 1/2001 | Zablocki et al. | |
| 6,348,032 B1 | 2/2002 | Sperl et al. | |
| 6,352,985 B1 | 3/2002 | Yamasaki et al. | |
| 6,387,939 B1 | 5/2002 | Assmann et al. | |
| 6,440,973 B1 | 8/2002 | Zablocki et al. | |
| 6,534,535 B1 | 3/2003 | Zhu et al. | |
| 6,605,634 B2 | 8/2003 | Zablocki et al. | |
| 6,638,960 B2 | 10/2003 | Assmann et al. | |

(Continued)

FOREIGN PATENT DOCUMENTS

| | | |
|---|---|---|
| EP | 0429257 A2 | 5/1991 |
| EP | 0882718 A1 | 12/1998 |

(Continued)

OTHER PUBLICATIONS

International Search Report from PCT/CN2012/071017, dated May 24, 2012.

(Continued)

*Primary Examiner* — Rita J Desai
(74) *Attorney, Agent, or Firm* — Dechert LLP

(57) ABSTRACT

The present invention relates to compounds according to Formula I and pharmaceutically acceptable salts thereof. Such compounds can be used in the treatment of RORgammaT-mediated diseases or conditions.

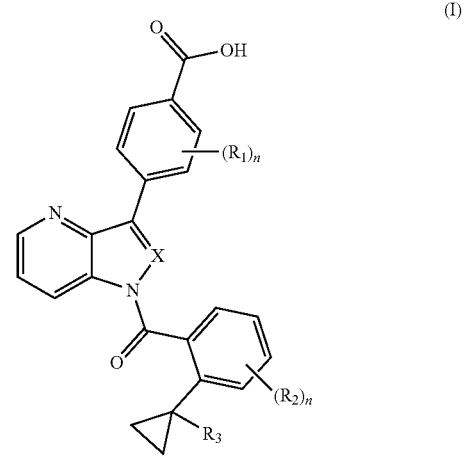

23 Claims, No Drawings

(56) References Cited

U.S. PATENT DOCUMENTS

| | | |
|---|---|---|
| 6,683,091 B2 | 1/2004 | Asberom et al. |
| 6,828,344 B1 | 12/2004 | Seehra et al. |
| 7,084,176 B2 | 8/2006 | Morie et al. |
| 7,115,750 B1 | 10/2006 | Kato et al. |
| 7,138,401 B2 | 11/2006 | Kasibhatla et al. |
| 7,329,675 B2 | 2/2008 | Cox et al. |
| 7,355,042 B2 | 4/2008 | Edgar et al. |
| 7,420,059 B2 | 9/2008 | O'Connor et al. |
| 7,482,342 B2 | 1/2009 | D'Orchymont et al. |
| 7,514,465 B2 | 4/2009 | Kuo et al. |
| 7,569,571 B2 | 8/2009 | Dong et al. |
| 7,696,200 B2 | 4/2010 | Ackermann et al. |
| 7,696,229 B2 | 4/2010 | Dunn et al. |
| 7,713,996 B2 | 5/2010 | Ackermann et al. |
| 7,741,495 B2 | 6/2010 | Liou et al. |
| 7,772,252 B2 | 8/2010 | Hendrix et al. |
| 7,799,933 B2 | 9/2010 | Ceccarelli et al. |
| 9,095,583 B2 * | 8/2015 | Karstens ............... C07D 231/56 |
| 9,266,827 B2 | 2/2016 | Aicher et al. |
| 9,273,070 B2 | 3/2016 | Knochel et al. |
| 9,487,490 B2 | 11/2016 | Barr et al. |
| 9,512,111 B2 | 12/2016 | Glick et al. |
| 9,556,168 B2 | 1/2017 | Barr et al. |
| 9,603,838 B2 | 3/2017 | Karstens et al. |
| 9,657,033 B2 | 5/2017 | Aicher et al. |
| 9,663,522 B2 | 5/2017 | Barr et al. |
| 9,745,265 B2 * | 8/2017 | Barr ..................... C07D 231/56 |
| 9,884,043 B2 | 2/2018 | Karstens et al. |
| 2006/0004000 A1 | 1/2006 | D'Orchymont et al. |
| 2006/0030612 A1 | 2/2006 | Steffan et al. |
| 2006/0100218 A1 | 5/2006 | Ibrahim et al. |
| 2006/0100230 A1 | 5/2006 | Bischoff et al. |
| 2007/0010537 A1 | 1/2007 | Hamamura et al. |
| 2007/0010670 A1 | 1/2007 | Hirata et al. |
| 2007/0049556 A1 | 3/2007 | Zhang et al. |
| 2007/0060567 A1 | 3/2007 | Ackermann et al. |
| 2007/0154487 A1 | 7/2007 | Littman et al. |
| 2007/0191603 A1 | 8/2007 | Ackermann et al. |
| 2007/0197782 A1 | 8/2007 | Clough et al. |
| 2007/0281922 A1 | 12/2007 | Liu et al. |
| 2008/0027100 A1 | 1/2008 | McCormick et al. |
| 2008/0058386 A1 | 3/2008 | Liou et al. |
| 2008/0153805 A1 | 6/2008 | Ceccarelli et al. |
| 2008/0305169 A1 | 12/2008 | Miki et al. |
| 2009/0005410 A1 | 1/2009 | Charvat et al. |
| 2009/0075973 A1 | 3/2009 | Newcom et al. |
| 2009/0124616 A1 | 5/2009 | Song et al. |
| 2009/0233955 A1 | 9/2009 | Frazee et al. |
| 2009/0247502 A1 | 10/2009 | Newcom et al. |
| 2009/0275586 A1 | 11/2009 | Govek et al. |
| 2010/0022515 A1 | 1/2010 | Alper et al. |
| 2010/0130484 A1 | 5/2010 | Ackermann et al. |
| 2010/0234340 A1 | 9/2010 | Schunk et al. |
| 2010/0317863 A1 | 12/2010 | Kuzmich et al. |
| 2011/0053915 A1 | 3/2011 | Ivaschenko et al. |
| 2011/0112070 A1 | 5/2011 | Baldwin et al. |
| 2011/0118246 A1 | 5/2011 | Baldwin et al. |
| 2011/0130384 A1 | 6/2011 | Setoh et al. |
| 2011/0150864 A1 | 6/2011 | Bignan et al. |
| 2011/0178063 A1 | 7/2011 | Baldwin et al. |
| 2011/0263046 A1 | 10/2011 | Deuschle et al. |
| 2014/0088094 A1 | 3/2014 | Glick et al. |
| 2015/0111877 A1 | 4/2015 | Aicher et al. |
| 2015/0126493 A1 | 5/2015 | Aicher et al. |
| 2015/0191434 A1 | 7/2015 | Barr et al. |
| 2015/0210687 A1 | 7/2015 | Barr et al. |
| 2015/0218096 A1 | 8/2015 | Barr et al. |
| 2015/0218169 A1 | 8/2015 | Barr et al. |
| 2015/0297566 A1 | 10/2015 | Karstens et al. |
| 2016/0304476 A1 | 10/2016 | Aicher et al. |
| 2016/0304505 A1 | 10/2016 | Aicher et al. |
| 2016/0311787 A1 | 10/2016 | Aicher et al. |
| 2017/0313722 A1 | 11/2017 | Aicher et al. |
| 2017/0340610 A1 | 11/2017 | Karstens et al. |
| 2018/0016239 A1 | 1/2018 | Lapointe et al. |
| 2018/0022701 A1 | 1/2018 | Barr et al. |
| 2018/0305320 A1 | 10/2018 | Lapointe et al. |
| 2018/0312489 A1 | 11/2018 | Lapointe et al. |

FOREIGN PATENT DOCUMENTS

| | | |
|---|---|---|
| EP | 1820515 A1 | 8/2007 |
| EP | 2181710 A1 | 5/2010 |
| EP | 2487159 A1 | 8/2012 |
| JP | 6-250441 A | 9/1994 |
| JP | 2004307487 A | 11/2004 |
| JP | 2007238463 A | 9/2007 |
| JP | 2016-141632 A | 8/2016 |
| WO | WO-92/13856 A1 | 8/1992 |
| WO | WO-1996/37467 A1 | 11/1996 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/012600 A1 | 2/2001 |
| WO | WO-02/100819 A1 | 12/2002 |
| WO | WO-03/014075 A2 | 2/2003 |
| WO | WO-2004/056830 A1 | 7/2004 |
| WO | WO-05/028434 A2 | 3/2005 |
| WO | WO-2005/037834 A1 | 4/2005 |
| WO | WO-2006/007486 A2 | 1/2006 |
| WO | WO-2006/026754 A2 | 3/2006 |
| WO | WO-2006/052190 A1 | 5/2006 |
| WO | WO-2006/057460 A1 | 6/2006 |
| WO | WO-2006/063167 A1 | 6/2006 |
| WO | WO-2007/024944 A1 | 3/2007 |
| WO | WO-2007/031429 A1 | 3/2007 |
| WO | WO-2007/093507 A1 | 8/2007 |
| WO | WO-2007/103308 A2 | 9/2007 |
| WO | WO-2007/125405 A2 | 11/2007 |
| WO | WO-2007/138998 A1 | 12/2007 |
| WO | WO-2007/144327 A2 | 12/2007 |
| WO | WO-2008/003703 A1 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/132434 A2 | 11/2008 |
| WO | WO-2008/138889 A2 | 11/2008 |
| WO | WO-2008/150827 A1 | 12/2008 |
| WO | WO-2008/153858 A1 | 12/2008 |
| WO | WO-2009/015067- | 1/2009 |
| WO | WO-2009/032667 A1 | 3/2009 |
| WO | WO-2009/035997 A2 | 3/2009 |
| WO | WO-2009/077956 A2 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/038901 A1 | 4/2010 |
| WO | WO-2010/50837 A1 | 5/2010 |
| WO | WO-2010/057101 A2 | 5/2010 |
| WO | WO-2010/059602 A2 | 5/2010 |
| WO | WO-2010/068483 A2 | 6/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2010/150837 A1 | 12/2010 |
| WO | WO-2011/014775 A1 | 2/2011 |
| WO | WO-2011/14775 A1 | 2/2011 |
| WO | WO-2011/019634 A2 | 2/2011 |
| WO | WO-2011/059839 A1 | 5/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/103189 A1 | 8/2011 |
| WO | WO-2011/109059 A1 | 9/2011 |
| WO | WO-2011/146313 A1 | 11/2011 |
| WO | WO-2012/032065 A1 | 3/2012 |
| WO | WO-2012/032067 A1 | 3/2012 |
| WO | WO-2012/037108 A1 | 3/2012 |

(56) References Cited

FOREIGN PATENT DOCUMENTS

| | | | |
|---|---|---|---|
| WO | WO-2012/064744 A2 | 5/2012 | |
| WO | WO-2012/077932 A2 | 6/2012 | |
| WO | WO-2012/106995 A1 | 8/2012 | |
| WO | WO-2012106995 A1 * | 8/2012 | ............ C07D 231/56 |
| WO | WO-2012/139775 A1 | 10/2012 | |
| WO | WO-2012/176763 A1 | 12/2012 | |
| WO | WO-2013/169704 A2 | 11/2013 | |
| WO | WO-2014/026327 A1 | 2/2014 | |
| WO | WO-2014/026329 A1 | 2/2014 | |
| WO | WO-2014/028589 A2 | 2/2014 | |
| WO | WO-2014/028591 A2 | 2/2014 | |
| WO | WO-2014/028597 A2 | 2/2014 | |
| WO | WO-2014/028600 A2 | 2/2014 | |
| WO | WO-2014028589 A2 * | 2/2014 | ............ C07D 231/56 |
| WO | WO-2015/008234 A1 | 1/2015 | |
| WO | WO-2015/087234 A1 | 6/2015 | |
| WO | WO-2015/139621 | 9/2015 | |
| WO | WO-2016/128908 A1 | 8/2016 | |
| WO | WO-2016/130818 A1 | 8/2016 | |

OTHER PUBLICATIONS

Bundgaard (ed.). Design of Prodrugs, Elsevier (1985).
Buonocore et al., "Innate lymphoid cells drive interleukin-23-dependent innate intestinal pathology," 464 Nature 1371-75 (2010).
Cheng et al., "Design and synthesis of heterocyclic malonyl-CoA decarboxylase inhibitors," 16 Bioorg. Med. Chem. Lett. 695-700 (2006).
Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).
Gennaro (ed.), Remington: The Science and Practice of Pharmacy, 20th edition (2000).
Higuchi et al. (eds.), Pro-drugs as Novel Delivery Systems, 14 A.C.S. Symposium Series (1975).
Hueber et al., "Cutting Edge: Mast Cells Express IL-17A in Rheumatoid Arthritis Synovium," 184 J. Immunol. 3336-40 (2010).
Jia et al., "The T helper type 17/regulatory T cell imbalance in patients with acute Kawasaki disease," 162 Clin. Exp. Immunol. 131-37 (2010).
Kastelein et al., "Discovery and Biology of IL-23 and IL-27: Related but Functionally Distinct Regulators of Inflammation," 25 Annu. Rev. Immunol. 221-42 (2007).
Louten et al., "Development and function of TH17 cells in health and disease," 123(5) J. Allergy Clin. Immunol. 1004-11 (2009).
Roche (ed.), Bioreversible Carriers in Drug Design, Pergamon Press (1987).
Zhou et al., "Use of Homogeneous Time-Resolved Fluorescence Energy Transfer in the Measurement of Nuclear Receptor Activation," 25 Methods 54-61 (2001).
Extended European Search Report, EP Application No. 12744370.3, dated Sep. 9, 2014.
Ciattini et al., "An Efficient Synthesis of 3-Substituted Indoles by Palladium-Catalyzed Coupling Reaction of 3-Tributylstannylindoles with Organic Triflates and Halides," 35(15) Tetrahedron Letters 2405-08 (1994).
Inamoto et al., "Palladium-Catalyzed C—H Activation/Intramolecular Amination Reaction: A New Route to 3-Aryl/Alkylindazoles," 9(15) Org. Letts. 2931-34 (2007).
Larhed et al., "Rapid Microwave-Assisted Suzuki Coupling on Solid-Phase," 37(45) Tetrahedron Letters 8219-22 (1996).
Reckenbeil et al., "Supramolekulare Phosphorylierung kationischer Alkohole mit 3-Arylindol-4-carboxamidin-Struktur," Liebigs Ann. Chem. 1219-29 (1994).
Chen, Hua-Sin et al., "Synthesis and antiplatelet activity of ethyl 4-(1-benzyl-1H-indazol-3-yl)benzoate (YD-3) derivatives," *Bioorganic & Medicinal Chemistry*, vol. 16, pp. 1262-1278, (2008).
Annunziato et al., "Type 17 T helper cells-origins, features and possible roles in rheumatic disease," 5 Nat. Rev. Rheumatol. 325-31 (2009).

Boaventura et al., "Human mucosal leishmaniasis: Neutrophils infiltrate areas of tissue damage that express high levels of Th17-related cytokines," 40 Eur. J. Immunol. 2830-36 (2010).
Eberl et al., "An essential function for the nuclear receptor RORγt in the generation of fetal lymphoid tissue inducer cells," 5(1) Nat. Immunol. 64-73 (2004).
He et al., "RORγt, a Novel Isoform of an Orphan Receptor, Negatively Regulates Fas Ligand Expression and IL-2 Production in T Cells," 9 Immunity 797-806 (1998).
Hirose et al., "RORγ: the third member of ROR/RZR orphan receptor subfamily that is highly expressed in skeletal muscle," 205 Biochem. Biophys. Res. Comm. 1976-83 (1994).
Ivanov et al., "The Orphan Nuclear Receptor RORγt Directs the Differentiation Program of Proinflammatory IL-17+ T Helper Cells," 126 *Cell* 1121-33 (2006).
Jin et al., "Structural Basis for Hydroxycholesterols as Natural Ligands of Orphan Nuclear Receptor RORγ," *Mol. Endocrinol.* (2010) vol. 24, No. 5, pp. 923-929.
Kurebayashi et al., "Selective LXXLL peptides antagonize transcriptional activation by the retinoid-related orphan receptor RORγ," 315 Biochem. Biophys. Res. Comm. 919-27 (2004).
Miossec et al., "Interleukin-17 and Type 17 Helper T Cells," 361(9) New Eng. J. Med. 888-98 (2009).
Sun et al., "Requirement for RORγ in Thymocyte Survival and Lymphoid Organ Development," 288 Science 2369-72 (2000).
Sutton et al., "Interleukin-1 and IL-23 Induce Innate IL-17 Production from γδ T Cells, Amplifying Th17 Responses and Autoimmunity," 31 Immunity 331-41 (2009).
Varnavas et al., "Anthranilic acid based CCK1 receptor antagonists: preliminary investigation on their second 'touch point,'" 40(6) Euro. J. Med. Chem. 563-81 (2005).
Wang et al., "Identification of SR1078, a Synthetic Agonist for the Orphan Nuclear Receptors RORα and RORγ," 5(11) ACS Chem. Biol. 1029-34 (2010).
Wang et al., "Modulation of Retinoic Acid Receptor-related Orphan Receptor α and γ Activity by 7-Oxygenated Sterol Ligands," *J. Biol. Chem.* (2010) vol. 285, No. 7, pp. 5013-5025.
Xie et al., "RORγt Recruits Steroid Receptor Coactivators to Ensure Thymocyte Survival," 175(6) J. Immunol. 3800-09 (2005).
Yang et al., "T Helper 17 Lineage Differentiation is programmed by Orphan Nuclear Receptors RORα and RORγ," 28 Immunity 29-39 (2008).
International Search Report and Written Opinion for PCT/US2013/054168, dated Feb. 14, 2014 (5 pages).
Lee et al., "Synthesis of 1-Benzyl-3-(5'-hydroxymethyl-2'-furyl)indazole Analogues as Novel Antiplatelet Agents," 44 J. Med. Chem. 3746-49 (2001).
André et al., "Disruption of retinoid-related orphan receptor β changes circadian behaviour, causes retinal degeneration and leads to vacillans phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Bernhardt et al., "Preparation of Solid Salt-Stabilized Functionalized Organozinc Compounds and their Application to Cross-Coupling and Carbonyl Addition Reactions," 50(39) Angew. Chem. Int. Ed. 9205-9209 (2011).
Boltze et al., "Chemische Struktur und antiphlogistische Wirkung in der Reihe der substituierten Indol-3-essigsauren," 30(8A) Arzneimittel-Forschung 1314-25 (1980).
Burris et al., "Targeting Orphan Nuclear Receptors for Treatment of Metabolic Diseases and Autoimmunity," 19(1) Chem. Biol. 51-59 (2012).
Cai, et al., "Pivotal Role of Dermal IL-17-Producing γδ T Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study

(56) References Cited

OTHER PUBLICATIONS of Active Psoriatic Arthritis" Arthritis & Rheumatology Brief Report, Accepted Article DOI: 10.1002/art.39685, American College of Rheumatology, (2016) pp. 1-27.
Baeten, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of *staggerer*," 70 Mech. Develop. 147-53 (1998).
Ei-Sawy et al., "Synthesis, antimicrobial and anti-cancer activities of some new N-ethyl, N-benzyl and N-benzoyl-3-indolyl heterocycles," 62 Acta Pharm. 157-179 (2012).
Giguère et al., "Isoform-specific amino-terminal domains dictate DNA-binding properties of RORα, a novel family of orphan hormone nuclear receptors," 8 Genes & Develop. 538-53 (1994).
Guo et al., "Stereospecific microbial reduction of ethyl 1-benzyl-3-oxo-piperidine-4-carboxylate," 17(13) Tetrahedron: Asymmetry 2015-2020 (2006).
Hirose et al., "Benzoheterocyclic derivatives. XI. Synthesis and pharmacological actions of indoline derivatives. 2," CA76:46035 (1971).
Huh et al., "Small molecule inhibitors of RORγt: Targeting Th17 cells and other applications," 42 Eur. J. Immunol. 2232-2237 (2012).
Julia et al., "Research in the indole series. IX. Certain 3-indolylsuccinic acids and the corresponding succinimides and pyrrolidines," CA61:92261 (1964).
Krueger, "A welcome surprise in psoriasis", Nature Medicine, (2012) vol. 18, No. 12, pp. 1750-1751.
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.
Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.
Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Skepner, J. et al. "Pharmacologic Inhibition of RORγt Regulates Th17 Signature Gene Expression and Suppresses Cutaneous Inflammation In Vivo," downloaded from the Internet at http://www.jimmunol.org/cgi/doi/10.4049/jimmunol.1302190 on Feb. 17, 2014, published in final edited form in *J. Immunol.* (2014) vol. 192, No. 6, pp. 2564-2575.
Smith, "The Bench-to-Bedside Story of IL-17 and the Therapeutic Efficacy of its Targeting in Spondyloarthritis", Curr Rheumatol Rep. (2016) vol. 18, pp. 1-10.
Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).

Whelligan et al., "Aminopyrazine Inhibitors Binding to an Unusual Inactive Conformation of the Mitotic Kinase Nek2: SAR and Structural Characterization," 53 J. Med. Chem. 7682-98 (2010).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
International Search Report and Written Opinion for PCT/US2013/054887, dated Mar. 18, 2014 (5 pages).
International Search Report and Written Opinion for PCT/US2013/054902, dated Feb. 28, 2014 (5 pages).
International Search Report and Written Opinion for PCT/US2013/054911 dated Mar. 4, 2014 (9 pages).
Database Caplus [Online] Chemical Abstracts Service, Columbus, Ohio, US; Kusakabe, Kanekazu et al: "Preparation of condensed pyrazole compounds as TTK protein kinase inhibitors", retrieved from STN Database accession No. 2011:1578140 ; & Kusakabe, Kanekazu et al: "Preparation of condensed pyrazole compounds as TTK protein kinase inhibitors", Jpn. Kokai Tokkyo Koho, 134PP. Coden: JKXXAF.
Arisawa et al., "Development of Isomerization and Cycloisomerization with Use of a Ruthenium Hydride with N-Heterocyclic Carbene and Its Application to the Synthesis of Heterocycles," 71 J. Org. Chem. 4255-61 (2006).
Berge et al., "Pharmaceutical salts," 66(1) J. Pharm. Sci. 1-19 (1977).
Bhagawanth et al., "Room-Temperature Pd-Catalyzed Amidation of Aryl Bromides Using tert-Butyl Carbamate," 74 J. Org. Chem. 4634-37 (2009).
Boger et al., "Regiocontrolled Nucleophilic Addition to Selectively Activated p-Quinone Diimines: Alternative Preparation of a Key Intermediate Employed in the Preparation of the CC-1065 Left-Hand Subunit," 55 J. Org. Chem. 1379-90 (1990).
Carroll et al., "Synthesis, Nicotinic Acetylcholine Receptor Binding, and Antinociceptive Properties of 2-exo-2-(2',3'-Disubstituted 5'-pyridinyl)-y-azabicyclo[2.2.1]heptanes: Epibatidine Analogues," 45 J. Med. Chem. 4755-61 (2002).
Chang et al., "7-Aroyl-aminoindoline-1-sulfonamides as a Novel Class of Potent Antitubulin Agents," 49 J. Med. Chem. 6656-59 (2006).
Colbon et al., "Double Arylation of Allyl Alcohol via a One-Pot Heck Arylation—Isomerization—Acylation Cascade," 13 Org. Lett. 5456-59 (2011).
De et al., Methods in Molecular Biology 1184, second edition, Human Press (2014).
Gould, "Salt selection for basic drugs," 33 Int'l J. Pharmaceutics 201-217 (1986).
Grasa et al., "Amination Reactions of Aryl Halides with Nitrogen-Containing Reagents Mediated by Palladium/Imidazolium Salt Systems," 66 J. Org. Chem. 7729-37 (2001).
Greene & Wuts, Protective Groups in Organic Synthesis, 2d Edition (1991).
Guimond et al., "Rhodium(III)-Catalyzed Isoquinolone Synthesis: The N—O Bond as a Handle for C—N Bond Formation and Catalyst Turnover," 132(20) J. Am. Chem. Soc. 6908-09 (2010).
Hanessian et al., "A versatile protocol for the stereocontrolled elaboration of vicinal secondary and tertiary centers of relevance to natural product synthesis," 52(6) J. Org. Chem. 1170-72 (1987).
Hauser et al., "Relative Ease of Cyclization of 2-, 3-, and 4-Aminopyridine Derivatives. Synthesis of Naphthyridines," 15 J. Org. Chem. 1224-32 (1950).
International Search Report and Written Opinion for PCT/US2011/059788 dated May 23, 2012 (23 pages).
International Search Report and Written Opinion for PCT/US2013/039422 dated Oct. 11, 2013 (9 pages).
International Search Report and Written Opinion for PCT/US2013/039839 dated Oct. 18, 2013 (8 pages).
International Search Report and Written Opinion for PCT/US2013/040085 dated Oct. 23, 2013 (9 pages).

(56) References Cited

OTHER PUBLICATIONS

Ishikura et al., "An Efficient Synthesis of 3-Heteroarylpyridines via Diethyl-(3-pyridyl)-borane," Synthesis 936-38 (1984).
Jayashree et al., "Design and synthesis of 2-quinolones as antioxidants and antimicrobials: a rational approach," 19 Med. Chem. Res. 193-209 (2010).
Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).
Li et al., "Chemical Libraries via Sequential C—H Functionalization of Phenols," 10 J. Comb. Chem. 170-74 (2008).
Li et al., "Synthesis and Resolution of a Novel Chiral Diamine Ligand and Application to Asymmetric Lithiation-Substitution," 2 Org. Lett. 875-78 (2000).
Liu et al., "1-Sulfonylindazoles as potent and selective 5-HT6 ligands," 19 Bioorg. Med. Chem. Lett. 2413-15 (2009).
Murase et al., "A New Concise Synthesis of Arcyriacyanin A and Its Unique Inhibitory Activity against a Panel of Human Cancer Cell Line," 48(1) Chem. Pharm. Bull. 81-84 (2000).
Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).
Nyrkova et al., "Synthesis of a New Heterocyclic System—3,4-Diazaphenoxazine," 1(9) J. Org. Chem. USSR, 1711-14, translating 1(9) Zh. Org. Khimii, 1688-91 (1965).
Santilli et al., "Synthesis of 5,6,7,8-Tetrahydro-5-oxopyrido[2,3-d] pyrimidine-6-carbonitriles and -6-carboxylic Acid Esters," 12 J. Het. Chem. 311-16 (1975).
Skraup, "Eine Synthese des Chinolins," 13 Berichte 2086-87 (1880).
Stefko et al., "General and Modular Synthesis of Isomeric 5-Substituted Pyridin-2-yl and 6-Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).
STN Columbus, pp. 1-40 (2011).
Takano et al., "A new synthesis of a steroid side chain via stereocontrolled protonation: synthesis of (-)-desmosterol," 14 J. Chem. Soc., Chem. Commun. 760-61 (1983).
Van Heerden et al., "Dibutylboron triflate promoted conjugate addition of benzylic and allylic organocopper reagents to chiral α,β-unsaturated N-acyl imidazolidinones" 38(10) Tet. Lett. 182-124 (1997).
Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).

Yeh et al., "Practical Cu-catalyzed amination of functionalized heteroaryl halides," 47(34) Tetrahedron Lett. 6011-16 (2006).
Zhu et al., "The Direct Formulation of Functionalized Alkyl(aryl)zinc halides by Oxidative Addition of Highly Reactive Zinc with Organic Halides and Their Reactions with Acid Chlorides, α,β-Unsaturated Ketones, and Allylic, Aryl, and Vinyl Halides," 56 J. Org. Chem. 1445-53 (1991).
International Search Report and Written Opinion for PCT/US2014/071671 dated Apr. 28, 2015 (10 pages).
International Search Report and Written Opinion for PCT/US2014/071663 dated Apr. 17, 2015 (6 pages).
International Search Report and Written Opinion for PCT/US2014/071656 dated Mar. 12, 2015 (8 pages).
International Search Report and Written Opinion for PCT/US2016/017566 dated May 6, 2016 (12 pages).
International Search Report and Written Opinion for PCT/US2016/059057 dated Dec. 9, 2016 (13 pages).
International Search Report and Written Opinion for PCT/US2016/059063 dated Jan. 20, 2017 (12 pages).
International Search Report and Written Opinion for PCT/US2016/059067 dated Jan. 11, 2017 (10 pages).
CAS Registry Nos. 886371-27-3 and 886370-74-7, STN entry date: Jun. 1, 2006.
Fauber Benjamin P. "Modulators of the Nuclear Receptor Retinoic Acid Receptor-Related Orphan Receptor-[gamma] (ROR[gamma] or RORc," *Journal of Medicinal Chemistry*, vol. 57, No. 14, Jul. 24, 2014 (Jul. 24, 2014), pp. 5871-5892, XP055242989.
Fauber Benjamin P. "Discovery of Imidazo[1,5-a]pyridines and -pyrimidines as potent and selective RORc inverse agonists," *Bioorganic & Medical Chemistry Letters*, vol. 25, No. 15, May 28, 2015 (May 28, 2015), pp. 2907-2912, XP029160601.
International Search Report and Written Opinion for PCT/US2013/054893 dated Feb. 24, 2014 (6 pages).
U.S. Appl. No. 15/647,437, 4-Heteroaryl Substituted Benzoic Acid Compounds as Rorgammat Inhibitors and Uses Thereof, filed Jul. 12, 2017.
U.S. Appl. No. 15/549,465, Substituted Pyrazole Compounds as RORgammaT Inhibitors and Uses Thereof, filed Aug. 8, 2017.
U.S. Appl. No. 15/770,255, Substituted Bicyclic Pyrazole Compounds as RORgammaT Inhibitors and Uses Thereof, filed Apr. 23, 2018.
U.S. Appl. No. 15/770,256, Substituted Indazole Compounds as RORgammaT Inhibitors and Uses Thereof, filed Apr. 23, 2018.

* cited by examiner

HETEROARYL SUBSTITUTED BENZOIC ACIDS AS RORGAMMAT INHIBITORS AND USES THEREOF

CROSS REFERENCE TO RELATED APPLICATIONS

This application is the national stage of International (PCT) Patent Application Serial No. PCT/US2016/059067, filed Oct. 27, 2016, which claims the benefit of and priority to U.S. Provisional Patent Application Ser. No. 62/246,915, filed Oct. 27, 2015, the contents of each of which are hereby incorporated by reference.

BACKGROUND OF THE INVENTION

Upon activation by antigen-presenting cells naïve T helper cells undergo clonal expansion and will ultimately differentiate into cytokine secreting effector T cells, such as Th1 and Th2 subtypes. A third and distinct effector subset has been identified, which plays a key role in providing immunity to bacteria and fungi at mucosal surfaces (Kastelein et al., *Annu. Rev. Immunol.* 25: 221-242, 2007). This effector T helper cell subset can be distinguished based on its ability to produce large quantities of IL-17/F, IL-21 and IL-22, and is named Th17 (Miossec et al., *New Eng. J. Med.* 2361: 888-898, 2009).

Different T helper subsets are characterized by the expression of lineage specific master transcription factors. Th1 and Th2 effector cells express T-bet and GATA3, respectively. A Thymocyte/T cell specific variant of Retinoic Acid Receptor-related Orphan Receptor (ROR), RORgammaT, is highly expressed in Th17 cells (He et al., *Immunity* 9: 797-806, 1998). RORgammaT belongs to the nuclear hormone receptor superfamily (Hirose et al., *Biochem. Biophys. Res. Comm.* 205: 1976-1983, 1994). RORgammaT is a truncated form of RORgamma, lacking the first N-terminal 21 amino acids and is, in contrast to RORgamma which is expressed in multiple tissues (heart, brain, kidney, lung, liver, and muscle), exclusively expressed in cells of the lymphoid lineage and embryonic lymphoid tissue inducers (Sun et al., *Science* 288: 2369-2372, 2000; Eberl et al., *Nat. Immunol.* 5: 64-73, 2004).

Studies using heterozygous knock-in mice replacing the RORgammaT open reading frame with GFP (green fluorescent protein) revealed a constitutive expression of GFP in approximately 10% of the CD4+ T cells in the small intestinal lamina propria (LP), co-expressing the Th17 cytokines IL-17/F and IL-22 (Ivanov et al., *Cell* 126: 1121-1133, 2006). In mice deficient for RORgammaT, the number of Th17 cells was markedly decreased in the LP; and in vitro stimulation of CD4+ T cells under Th17 polarizing conditions resulted in a drastic decrease of IL-17 expression. These results were further substantiated via forced expression of RORgammaT in naïve CD4+ T cells, which resulted in an induction of IL-17/F and IL-22 (Ivanov et al., *Cell* 126: 1121-1133, 2006). The foregoing studies demonstrate the importance of RORgammaT in differentiation and stabilization of the Th17 lineage. In addition, a ROR family member, RORalpha, has been demonstrated to be involved in Th17 differentiation and stabilization (Yang et al., *Immunity* 28: 29-39, 2008).

Recently, RORgammaT was shown to play a crucial role in non-Th17 lymphoid cells. In these studies, RORgammaT was critically important in innate lymphoid cells expressing Thy1, SCA-1, and IL-23R proteins. Genetic disruption of RORgamma in a mouse colitis model dependent on these innate lymphoid cells prevented colitis development (Buonocore et al., *Nature* 464: 1371-1375, 2010). In addition, RORgammaT was shown to play a crucial role in other non-Th17 cells, such as mast cells (Hueber et al., *J. Immunol.* 184: 3336-3340, 2010). Finally, RORgammaT expression and secretion of Th17-type of cytokines was reported for Lymphoid Tissue Inducer cells, NK T-cells, NK cells (Eberl et al., *Nat. Immunol.* 5: 64-73, 2004), and gamma-delta T-cells (Sutton et al., *Nat. Immunol.* 31: 331-341, 2009; Louten et al., *J. Allergy Clin. Immunol.* 123: 1004-1011, 2009), suggesting an important function for RORgammaT in these subtypes of cells.

Based on the role of IL-17 producing cells (either Th17 or non-Th17 cells), RORgammaT has been identified as a key mediator in the pathogenesis of several diseases (Louten et al., *J. Allergy Clin. Immunol.* 123: 1004-1011, 2009; Annuziato et al., *Nat. Rev. Rheumatol.* 5: 325-331, 2009). This was confirmed using several disease models representative of autoimmune diseases. Genetic ablation of the RORgamma gene in mice prevented the development of experimental autoimmune diseases, such as experimental autoimmune encephalomyelitis (EAE) and colitis (Ivanov et al., *Cell* 126:1121-33, 2006; Buonocore et al., *Nature* 464: 1371-1375, 2010).

With RORgammaT being a critical mediator in Th17 cells and non-Th17 cells, antagonism of the transcriptional activity of RORgammaT is expected to have a beneficial effect on autoimmune diseases such as, but not limited to, rheumatoid arthritis, psoriasis, multiple sclerosis, inflammatory bowel disease, Crohn's disease, and asthma (Annunziato et al., *Nat. Rev. Immunol.* 5: 325-331, 2009; Louten et al., *J. Allergy Clin. Immunol.* 123: 1004-1011, 2009). Antagonism of RORgammaT may also be beneficial in other diseases that are characterized by increased levels of Th17 cells and/or elevated levels of Th17 hallmark cytokines such as IL-17, IL-22 and IL-23. Examples of such diseases are Kawasaki Disease (Jia et al., *Clin. Exp. Immunol.* 162: 131-137, 2010) and Hashimoto's thyroiditis (Figueroa-Vega et al., *J. Clin. Endocrinol. Metab.* 95: 953-962, 2010). Other examples include various infectious diseases such as, but not limited to, mucosal leishmaniasis (Boaventura et al., *Eur. J. Immunol.* 40: 2830-2836, 2010). In each of the above examples the inhibition may be enhanced by simultaneous inhibition of RORalpha.

Compounds modulating RORgammaT have been reported. Examples of agonists include T0901317 and SR1078 (Wang et al., *ACS Chem. Biol.* 5:1029-1034, 2010). In addition, antagonists have been reported such as 7-oxygenated sterols (Wang et al., *J. Biol. Chem.* 285: 5013-5025, 2009) and compounds described in EP2181710 A1.

Numerous immune and inflammatory disorders continue to afflict millions of patients worldwide. Although significant advances have been made in treating these disorders, current therapies do not provide satisfactory results for all patients due to, for example, detrimental side effects or insufficient efficacy. One exemplary immune disorder in need of better therapy is psoriasis. Various therapeutics have been developed in an attempt to treat psoriasis. However, the traditional therapies for psoriasis often have toxic adverse effects. An exemplary inflammatory disorder in need of better treatment is rheumatoid arthritis. Numerous therapeutics have been developed in an attempt to treat this disorder. However, some patients develop resistance to current therapies. Another exemplary disorder in need of better therapy is cancer.

Accordingly, a need exists for improved treatments for immune disorders and inflammatory disorders. The present invention addresses this need and provides other related advantages.

SUMMARY OF THE INVENTION

The present invention provides compounds that alter the interaction of coregulator proteins with RORgammaT (and thereby, as commonly observed for nuclear hormone receptors, antagonize RORgammaT-mediated transcriptional activity; see e.g. "Differential Biochemical and Cellular Actions of Premarin Estrogens: Distinct Pharmacology of Bazedoxifene-Conjugate Estrogens Combination". Berrodin, T. J., Chang, K. C. N., Komm, B. S., Freedman, L. P., Nagpal, S. Molecular Endrocrinology, January 2009, 23(1): 74-85) and are useful for the treatment of RORgammaT-mediated diseases or conditions, in particular autoimmune diseases and inflammatory diseases, as well as pharmaceutical compositions comprising such compounds and pharmaceutical carriers.

DETAILED DESCRIPTION OF THE INVENTION

Definitions

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure.

As used herein, and throughout this disclosure, the following terms, unless otherwise indicated, shall be understood to have the following meanings:

The term "alkyl" as used herein, refers to an aliphatic hydrocarbon group having one of its hydrogen atoms replaced with a bond having the specified number of carbon atoms.

In an embodiment, an alkyl group contains, for example, from 1 to 4 carbon atoms $(C_{1-4})$alkyl. Non-limiting examples of alkyl groups include methyl, ethyl, n-propyl, isopropyl, n-butyl, sec-butyl, isobutyl and tert-butyl. In one embodiment, an alkyl group is linear. In another embodiment, an alkyl group is branched.

The term "halogen" (or "halo") refers to fluorine, chlorine, bromine and iodine (alternatively referred to as fluoro (F), chloro (Cl), bromo (Br), and iodo (I)). In one embodiment, a halogen is F or Cl. In another embodiment, halogen is F.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

When any substituent or variable occurs more than one time in any constituent or in the compound of Formulas (I-III), its definition on each occurrence is independent of its definition at every other occurrence, unless otherwise indicated.

The term "purified" as used herein, refers to the physical state of a compound after the compound has been isolated through a synthetic process (e.g., from a reaction mixture), from a natural source, or a combination thereof. The term "purified" also refers to the physical state of a compound after the compound has been obtained from a purification process or processes described herein or well-known to the skilled artisan (e.g., chromatography, recrystallization, and the like), in sufficient purity to be characterizable by standard analytical techniques described herein or well-known to the skilled artisan.

The term "amount" or "effective amount" as used herein refers to an amount of the compound of Formulas (I-III) and/or an additional therapeutic agent, or a composition thereof, that is effective in producing the desired therapeutic, ameliorative, inhibitory or preventative effect when administered to a subject suffering from an RORgammaT-mediated disease or disorder. In the combination therapies of the present invention, as effective amount can refer to each individual agent or to the combination as a whole, wherein the amounts of all agents administered are together effective, but wherein the component agent of the combination may not be present individually in an effective amount.

A "subject" is a human or non-human mammal. In one embodiment, a subject is a human.

It should be noted that any carbon as well as heteroatom with unsatisfied valences in the text, schemes, examples and tables herein is assumed to have the sufficient number of hydrogen atom(s) to satisfy the valences.

Compounds of the Invention

The present invention provides a compound according to Formula I:

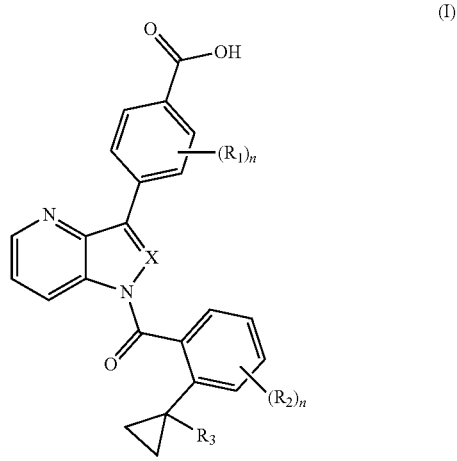

(I)

wherein:
X is CH or N;
n is 0, 1 or 2;
$R_1$ is independently OH, halo or $(C_{1-4})$alkyl;
$R_2$ is independently OH, halo, $(C_{1-4})$alkyl, $CH_2F$, $CHF_2$ or $CF_3$; and
$R_3$ is $CH_2F$, $CHF_2$ or $CF_3$;
or a pharmaceutically acceptable salt thereof.

A more specific collection of compounds may be described according to the following definitions for certain variables for Formula I. In certain embodiments, n is 1. In certain embodiments, $R_1$ is chloro or fluoro. In certain embodiments, $R_1$ is fluoro. In certain embodiments, $R_2$ is chloro or fluoro. In certain embodiments, $R_2$ is chloro. In certain embodiments, X is N. In certain embodiments, X is CH. In certain embodiments, $R_3$ is $CF_3$. In certain embodiments, the compound is in the form of a free acid. The invention embraces all combinations of such embodiments, such as where n is 1, $R_1$ is fluoro, $R_2$ is chloro, and X is N.

In another embodiment, the present invention provides a compound according to Formula II:

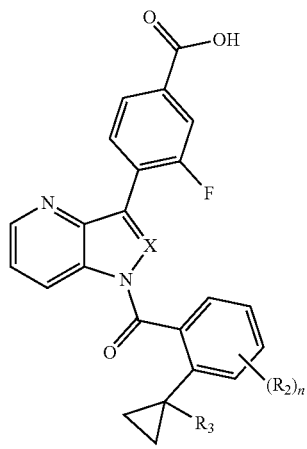

(II)

wherein:
X is CH or N;
n is 1 or 2;
$R_2$ is independently OH, halo, ($C_{1-4}$)alkyl, $CH_2F$, $CHF_2$ or $CF_3$; and
$R_3$ is $CH_2F$, $CHF_2$ or $CF_3$;
or a pharmaceutically acceptable salt thereof.

A more specific collection of compounds may be described according to the following definitions for certain variables for Formula II. In certain embodiments, n is 1. In certain embodiments, $R_2$ is chloro or fluoro. In certain embodiments, $R_2$ is chloro. In certain embodiments, X is N. In certain embodiments, X is CH. In certain embodiments, $R_3$ is $CF_3$. In certain embodiments, the compound is in the form of a free acid. The invention embraces all combinations of such embodiments, such as where n is 1, $R_2$ is chloro, and X is N.

In another embodiment, the present invention provides a compound according to Formula III:

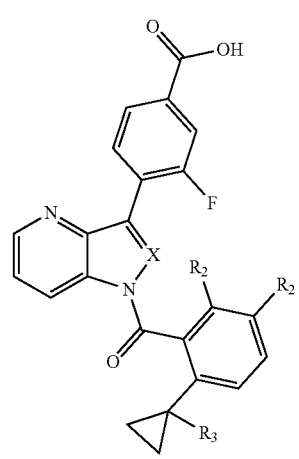

(III)

wherein:
X is CH or N;
$R_2$ is independently H, Cl, F, $CH_3$ or $CHF_2$; and
$R_3$ is $CH_2F$, $CHF_2$ or $CF_3$;
or a pharmaceutically acceptable salt thereof.

A more specific collection of compounds may be described according to the following definitions for certain variables for Formula III. In certain embodiments, $R_2$ is H or chloro. In certain embodiments, one $R_2$ is chloro and the other $R_2$ is hydrogen. In certain embodiments, $R_2$ is chloro or fluoro. In certain embodiments, $R_2$ is chloro. In certain embodiments, X is N. In certain embodiments, X is CH. In certain embodiments, $R_3$ is $CF_3$. In certain embodiments, the compound is in the form of a free acid. The invention embraces all combinations of such embodiments, such as where one $R_2$ is chloro and the other $R_2$ is hydrogen, $R_2$ is chloro, and X is N.

Exemplary specific compounds according to the instant invention include, for example:
3-fluoro-4-(1-(2-methyl-6-(1-(trifluoromethyl)cyclopropyl) benzoyl)-1H-pyrazolo[4,3-b]pyridin-3-yl)benzoic acid;
4-(1-(2-chloro-6-(1-(difluoromethyl)cyclopropyl)benzoyl)-1H-pyrazolo[4,3-b]pyridin-3-yl)-3-fluorobenzoic acid;
4-(1-(2-chloro-6-(1-(fluoromethyl)cyclopropyl)benzoyl)-1H-pyrazolo[4,3-b]pyridin-3-yl)-3-fluorobenzoic acid;
4-(1-(2-chloro-3-fluoro-6-(1-(trifluoromethyl)cyclopropyl) benzoyl)-1H-pyrazolo[4,3-b]pyridin-3-yl)-3-fluorobenzoic acid;
4-(1-(2-(difluoromethyl)-6-(1-(trifluoromethyl)cyclopropyl)benzoyl)-1H-pyrazolo[4,3-b]pyridin-3-yl)-3-fluorobenzoic acid;
4-(1-(2-chloro-6-(1-(difluoromethyl)cyclopropyl)-3-fluorobenzoyl)-1H-pyrazolo[4,3-b]pyridin-3-yl)-3-fluorobenzoic acid;
3-fluoro-4-(1-(3-fluoro-2-methyl-6-(1-(trifluoromethyl)cyclopropyl)benzoyl)-1H-pyrazolo[4,3-b]pyridin-3-yl)benzoic acid; and
4-(1-(2-chloro-6-(1-(trifluoromethyl)cyclopropyl)benzoyl)-1H-pyrrolo[3,2-b]pyridin-3-yl)-3-fluorobenzoic acid;
or a pharmaceutically acceptable salt thereof.

Collections of compounds defined by Formulae I, II, and III may be more specifically described according to the following embodiments specifying certain definitions (where present) for variables X, n, $R_1$, and $R_2$. In an embodiment, X is N. In an embodiment, X is CH. In an embodiment, n is 1 or 2. In an embodiment, $R_1$ is independently F and $CH_3$. In an embodiment, $R_1$ is F. In an embodiment, each $R_2$ is independently H, Cl, F, $CH_3$, $CH_2F$, $CHF_2$ or $CF_3$. In an embodiment, each $R_2$ is independently H, Cl, F, $CH_3$ or $CHF_2$.

The invention also provides a compound of Formulas I-III, or a pharmaceutically acceptable salt thereof in purified form.

In certain embodiments, a compound of Formula I, II, or III is provided in the form of a free base or free acid (i.e., not a salt form).

The invention includes prodrugs, hydrates or solvates of the compounds described herein. The use of the terms "prodrug", "hydrate", "salt", "solvate", "ester", and the like is intended to equally apply to the salt, solvate, ester, and prodrug of enantiomers, stereoisomers, rotamers, tautomers, positional isomers, racemates, or prodrugs of the inventive compounds.

Optical Isomers—Diastereomers—Geometric Isomers—Tautomers

The compounds of Formulas (I-III) may contain asymmetric or chiral centers, and, therefore, exist in different stereoisomeric forms. It is intended that all stereoisomeric forms of the compounds of Formulas (I-III) as well as mixtures thereof, including racemic mixtures, form part of the present invention. In addition, the present invention embraces all geometric and positional isomers. For example, if a compound of Formulas (I-III) incorporates a double bond or a fused ring, both the cis- and trans-forms, as well as mixtures, are embraced within the scope of the invention.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formulas (I-III) are shown without a definitive stereochemistry at certain positions. The present invention includes all stereoisomers of Formulas (I-III) and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formulas (I-III) may be obtained by stereospecific synthesis using optically pure starting materials or reagents of known configuration.

Some of the compounds of Formulas (I-III) may be atropisomers (e.g. substituted biaryls) and are considered as part of this invention.

When compounds described herein contain olefinic double bonds, unless specified otherwise, such double bonds are meant to include both E and Z geometric isomers.

Some of the compounds described herein may exist with different points of attachment of hydrogen. Such compounds are referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are included within the scope of the present invention. The compounds of Formulas I-III may exist in different tautomeric forms, and all such forms are embraced within the scope of the invention. Also, for example, imine-enamine forms of the compounds are included in the invention.

All stereoisomers (for example, geometric isomers, optical isomers and the like) of the present compounds (including those of the salts, solvates, esters, and prodrugs of the compounds as well as the salts, solvates, and esters of the prodrugs), such as those that may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (-ic and -ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

The compounds of Formulas I-III can form salts which are also within the scope of this invention. Reference to a compound of Formulas I-III herein is understood to include reference to salts thereof, unless otherwise indicated.

The term pharmaceutically acceptable salt represents those salts that are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide, calcium hydroxide, calcium carbonate, ammonium (e.g. diethylamine) or lithium hydroxide.

Solvates

The present invention includes within its scope solvates of compounds of Formulas (I-III). As used herein, the term "solvate" refers to a complex of variable stoichiometry formed by a solute (i.e., a compound of Formulas (I-III)) or a pharmaceutically acceptable salt thereof and a solvent that does not interfere with the biological activity of the solute. Examples of solvents include but are not limited to water, ethanol, and acetic acid. When the solvent is water, the solvate is known as hydrate; hydrate includes, but is not limited to, hemi-, mono, sesqui-, di- and trihydrates.

The compounds of the invention may form hydrates or solvates. It is known to those of skill in the art that charged compounds form hydrated species when lyophilized with water, or form solvated species when concentrated in a solution with an appropriate organic solvent. One or more compounds of the invention may exist in unsolvated as well as solvated forms with pharmaceutically acceptable solvents such as water, ethanol, and the like, and it is intended that the invention embrace both solvated and unsolvated forms. "Solvate" may also mean a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of Formulas I-III or with a compound that may not be a compound of Formulas I-III, but that converts to a compound of Formulas I-III in vivo after administration to the patient. Conventional procedures for the selection and preparation of suitable prodrug derivatives are described, for example, in "Design of Prodrugs," ed. H. Bundgaard, Elsevier, 1985.

The term "prodrug" means a compound (e.g., a drug precursor) that is transformed in vivo to yield a compound of Formulas I-III or a pharmaceutically acceptable salt, hydrate or solvate of the compound. The transformation may occur by various mechanisms (e.g., by metabolic or chemical processes), such as, for example, through hydrolysis in blood. A discussion of prodrugs and the use of prodrugs is provided by T. Higuchi and W. Stella, "Pro-drugs as Novel Delivery Systems," Vol. 14 of the A.C.S. Symposium Series, 1987; and in Bioreversible Carriers in Drug Design, ed. Edward B. Roche, American Pharmaceutical Association and Pergamon Press, 1987.

Isotopes

In the compounds of generic Formulas (I-III), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formulas I-III. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. In light of the present disclosure, isotopically-enriched compounds within generic Formulas (I-III) can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention alter the interaction of coregulator proteins with Retinoic Acid Receptor-related Orphan Receptor gamma t (RORgammaT) and thereby antagonize RORgammaT-mediated transcriptional activity, and as such are useful in the treatment of diseases and conditions in which inhibition of RORgammaT is desirable, such as autoimmune and inflammatory diseases and disorders.

Accordingly, another embodiment of the present invention provides a method for treating a disease or condition mediated by RORgammaT in a subject comprising administering to the subject an amount of a compound having Formulas I-III, or a pharmaceutically acceptable salt thereof, that is effective for treating the disease or condition mediated by RORgammaT in the subject.

The compounds according to the invention can be used in therapy.

A further aspect of the invention resides in the use of compounds according to the invention or a pharmaceutically acceptable salt thereof for the treatment of RORgammaT-mediated diseases or RORgammaT mediated conditions.

Another aspect of the invention resides in the use of compounds or a pharmaceutically acceptable salt thereof having the general Formulas (I-III) for the treatment of autoimmune diseases, in particular those diseases in which Th17 cells and non-Th17 cells, which express Th17 hallmark cytokines, play a prominent role. These include, but are not limited to, the treatment of rheumatoid arthritis, psoriasis, inflammatory bowel disease, Crohn's disease, ankylosing spondylitis and multiple sclerosis.

In another aspect, compounds or a pharmaceutically acceptable salt thereof having the general Formulas (I-III) can be used for treatment of inflammatory diseases in which Th17 cells and/or non-Th17 cells, which express Th17 hallmark cytokines, play a prominent role, such as but not limited to respiratory diseases, osteoarthritis and asthma. Also, compounds or a pharmaceutically acceptable salt thereof having the general Formulas (I-III) can be used for treatment of infectious diseases in which Th17 cells and/or non-Th17 cells, which express Th17 hallmark cytokines, play a prominent role, such as but not limited to mucosal leishmaniasis.

Accordingly, in certain embodiments, the invention provides a method of treating a disorder selected from the group consisting of an autoimmune disorder and an inflammatory disorder, where the method comprises administering to a subject in need thereof a therapeutically effective amount of a compound described herein (e.g., a compound of Formula I, II, or III) to treat the disorder. In certain embodiments, the disorder is an autoimmune disorder. In certain embodiments, the autoimmune disorder is rheumatoid arthritis, psoriasis, Crohn's disease, inflammatory bowel disease, multiple sclerosis, psoriasis, ankylosing spondylitis, systemic lupus erythematosus, chronic graft-versus-host disease, acute graft-versus-host disease, Celiac Sprue, idiopathic thrombocytopenic thrombotic purpura, myasthenia gravis, Sjogren's syndrome, scleroderma, ulcerative colitis, or epidermal hyperplasia. In certain other embodiments, the autoimmune disorder is rheumatoid arthritis, psoriasis, Crohn's disease, inflammatory bowel disease, multiple sclerosis, or psoriasis. In certain embodiments, the disorder is an inflammatory disorder. In certain embodiments, the inflammatory disorder is a respiratory disease or osteoarthritis. In certain other embodiments, the inflammatory disorder is osteoarthritis or asthma.

Compounds or a pharmaceutically acceptable salt thereof having the general Formulas (I-III) can also be used for treatment of other diseases in which Th17 cells and/or non-Th17 cells, which express Th17 hallmark cytokines, play a prominent role, such as but not limited to Kawasaki disease and Hashimoto's thyroiditis.

In one aspect the disease or condition is an autoimmune disease or an inflammatory disease. The disease or condition includes, but is not limited to, multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis or mucosal leishmaniasis.

In another aspect, the compounds according to the invention can be used in therapies to treat or prevent multiple sclerosis, inflammatory bowel disease, Crohn's disease, psoriasis, rheumatoid arthritis, asthma, osteoarthritis, Kawasaki disease, Hashimoto's thyroiditis and mucosal leishmaniasis.

In another aspect the compounds according to the invention can be used to treat or prevent psoriasis.

In yet another aspect the compounds according to the invention can be used to treat inflammatory bowel disease.

In yet another aspect the compounds according to the invention can be used to treat cancer. The term cancer includes, but is not limited to, colorectal, lung, and pancreatic cancer. Additional exemplary cancers contemplated for treatment include, for example, ovarian cancer, a melanoma, breast cancer, prostate cancer, renal cell carcinoma, testicular cancer, uterine cancer, brain cancer, bladder cancer, leukemia, a B-cell lymphoma, and non-Hodgkin lymphoma.

In another aspect the compounds according to the invention can be used to treat colorectal cancer.

In another aspect the compounds according to the invention can be used to treat lung cancer.

In another aspect the compounds according to the invention can be used to treat pancreatic cancer.

Another aspect of the invention provides a method of inhibiting the activity of RORγ. The method comprises exposing a RORγ to an effective amount of a compound described herein (e.g., a compound of Formula I, II, or III) to inhibit the activity of said RORγ.

Another aspect of the present invention further includes the use of a compound of Formulas I-III, or a pharmaceutically acceptable salt thereof, in the manufacture of a medicament for the treatment of a disease or condition mediated by RORgammaT.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration that include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., autoimmune and inflammatory diseases and disorders.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition, Lippincott Williams & *Wilkins*, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive that does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical Compositions

Another aspect of the present invention provides pharmaceutical compositions comprising a compound of Formulas (I-III), or a pharmaceutically acceptable salt thereof, and one or more pharmaceutically acceptable excipients or carriers. The term "excipient" and "carrier" may be used interchangeably. The term "composition", as in pharmaceutical composition, is intended to encompass a product comprising the active ingredient(s), and the inert ingredient(s) (pharmaceutically acceptable excipients) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formulas I-III, additional active ingredient(s), and pharmaceutically acceptable excipients.

The pharmaceutical compositions of the present invention comprise a compound represented by Formulas I-III (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragees, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formulas I-III in suitable propellants, such as fluorocarbons or hydrocarbons.

For ocular administration, an ophthalmic preparation may be formulated with an appropriate weight percent solution or suspension of the compounds of Formulas I-III in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules may be prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules may be washed and dried.

A large number of tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection may be prepared by stirring 1.5% by weight of active ingredient in 10% by volume propylene glycol. The solution may be made to volume with water for injection and sterilized.

An aqueous suspension may be prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The present invention also relates to a pharmaceutical composition comprising compounds or pharmaceutically acceptable salts thereof having the general Formulas I-III in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

Combination Therapy

Compounds of the present invention, and their salts and solvates, and physiologically functional derivatives thereof, may be employed alone or in combination with other therapeutic agents for the treatment of diseases and conditions associated with inappropriate IL-17 pathway activity. Combination therapies according to the present invention thus comprise the administration of at least one compound of formulas (I-III) or a pharmaceutically acceptable salt thereof, or a physiologically functional derivative thereof, and the use of at least one other pharmaceutically active agent. The compound(s) of formulas (I-III) and the other pharmaceutically active agent(s) may be administered together or separately and, when administered separately this may occur simultaneously or sequentially in any order. The amounts of the compound(s) of formulas (I-III) and the other pharmaceutically active agent(s) and the relative timings of administration will be selected in order to achieve the desired combined therapeutic effect. For the treatment of the inflammatory and autoimmune diseases, rheumatoid arthritis, psoriasis, inflammatory bowel disease, ankylosing spondylitis, SLE, uveitis, atopic dermatitis, COPD, asthma and allergic rhinitis a compound of Formulas (I-III) may be combined with one or more other active agents such as: (1) TNF-a inhibitors; (2) non-selective COX-I/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine HI receptor antagonists; (9) a1- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK 1 and/or JAK2 and/or JAK 3 and/or TYK2), p38 MAPK and IKK2; (15) B-cell targeting biologies such as rituximab; (16) selective costimulation modulators such as abatacept; (17) interleukin inhibitors, such as IL-1 inhibitor anakinra, IL-6 inhibitor tocilizumab, and IL12/IL-23 inhibitor ustekinumab. The compounds of the invention could also be combined with anti-IL17 antibodies to obtain additive/synergistic responses for the treatment of inflammatory and autoimmune diseases.

Compounds of the present invention, and their salts and solvates, and physiologically functional derivatives thereof, may be employed alone or in combination with other anti-cancer agents for the treatment of cancer.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

Methods of Synthesis

Methods for preparing the compounds of this invention are illustrated in the following schemes and examples. Other synthetic protocols will be readily apparent to those skilled in the art. The examples illustrate the preparation of the compounds of formula I and as such are not to be considered as limiting the invention set forth in the claims appended hereto. Unless otherwise indicated, all variables are as previously defined.

All the end products of formula I were analyzed by NMR and/or LCMS. Intermediates were analyzed by NMR and/or TLC and/or LCMS. Most compounds were purified by reverse phase HPLC, MPLC on silica gel, recrystallization and/or swish (suspension in a solvent followed by filtration of the solid). The course of the reactions was followed by thin layer chromatography (TLC) and/or LCMS and/or NMR and reaction times are given for illustration only.

Abbreviations used herein are as follows: EtOAc: Ethyl acetate; PE: Petroleum ether; DCM: Dichloromethane; dppf: 1,1'-Bis(diphenylphosphino) ferrocene; AcOH: Acetic acid; DMAC: N,N-Dimethylacetamide; Pd(PPh$_3$)$_4$: Tetrakis(Triphenylphosphine) Palladium(0); Pd(dppf)Cl$_2$: [1,1'-Bis(diphenyl phosphino) ferrocene]dichloro palladium (II); Ac$_2$O: Acetic anhydride; LiHMDS: Lithiumbis(trimethylsilyl)amide; PhNTf$_2$: N-Phenyl-bis(trifluoromethane sulfonimide); CPME: Cyclopentyl methyl ether; DMAP: 4-Dimethylaminopyridine; TEA: Triethylamine; THF: Tetrahydrofuran; DMP: Dess-Martin periodinane; DDQ: 2,3-Dichloro-5,6-Dicyanobenzoquinone; BPD: Bis(pinacolato)diboron; BINAP: 1,1'-Binaphthalene-2,2'-diyl)bis(diphenylphosphine; DIBAL-H: Diisobutylaluminium hydride; DAST: (Diethylamino)sulfur trifluoride.

Scheme 1 illustrates a general method toward the preparation of compounds of formula I. Starting from THP or Boc protected 3-halo-4-aza-indazole or indole A, Suzuki coupling, followed by deprotection under acidic conditions afforded free 4-aza-indazole or indole intermediate B. Coupling of intermediate B with various fluoromethylcyclopropyl substituted benzoyl chloride (derived from the corresponding benzoic acids), followed by ester hydrolysis furnished the desired final product I.

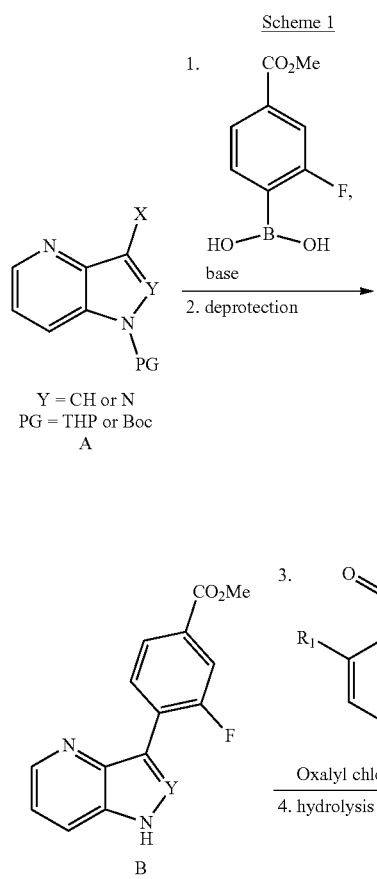

Intermediates:

Intermediate i-1

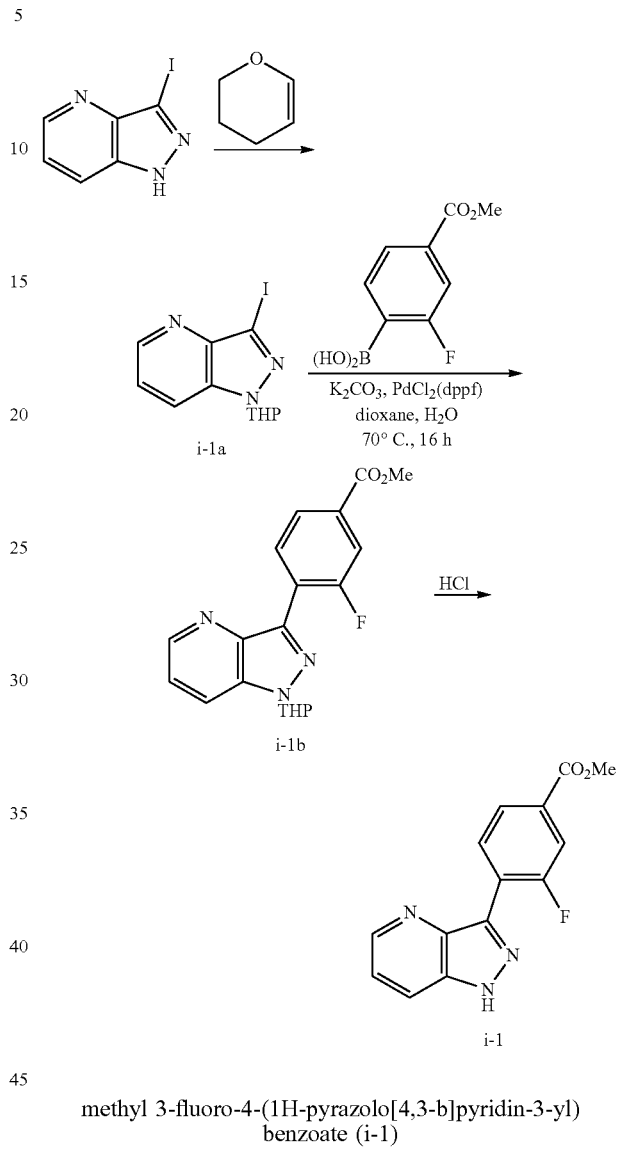

methyl 3-fluoro-4-(1H-pyrazolo[4,3-b]pyridin-3-yl)benzoate (i-1)

Step 1: Preparation of 3-iodo-1-(tetrahydro-2H-pyran-2-yl)-1H-pyrazolo[4,3-b]pyridine (i-1a)

To a mixture of 3-iodo-1H-pyrazolo[4,3-b]pyridine (10 g, 40.8 mmol) in THF (136 mL) were added 3,4-dihydro-2H-pyran (11.7 mL, 122 mmol) and 4-methylbenzenesulfonic acid (0.70 g, 4.1 mmol). The reaction mixture was stirred at 70° C. for 14 h, cooled down, poured into separation funnel containing sat. NaHCO$_3$, and extracted with EtOAc. The combined organics were washed with H$_2$O, brine, dried over Na$_2$SO$_4$, and concentrated. The crude residue was purified by flash chromatography (10-60% EtOAc/hexanes) to give the desired product. LCMS: 330 (M+1).

Step 2: Preparation of methyl 3-fluoro-4-(1-(tetrahydro-2H-pyran-2-yl)-1H-pyrazolo[4,3-b]pyridin-3-yl)benzoate (i-1b)

A mixture of 3-iodo-1-(tetrahydro-2H-pyran-2-yl)-1H-pyrazolo[4,3-b]pyridine i-1a (300 mg, 0.91 mmol), (2-fluoro-4-(methoxycarbonyl)phenyl)boronic acid (217 mg, 1.09 mmol), $K_2CO_3$ (252 mg, 1.82 mmol) and $PdCl_2$(dppf) (70 mg, 0.10 mmol) in dioxane (3.0 mL) and water (0.5 mL) was stirred at 70° C. for 16 h under nitrogen atmosphere. The reaction mixture was diluted with $H_2O$ and extracted with EtOAc. The combined organics were dried over $Na_2SO_4$, and concentrated. The crude residue was purified by column chromatography (5-20% EtOAc/hexanes) to afford the title compound as a solid. $^1H$ NMR (400 MHz, $CDCl_3$) δ 8.69 (d, J=3.6 Hz, 1H), 8.39 (t, J=7.4 Hz, 1H), 8.05 (d, J=8.4 Hz, 1H), 7.97 (d, J=8.0 Hz, 1H), 7.89 (d, J=10.8 Hz, 1H), 7.37-7.34 (m, 1H), 5.85 (dd, J=8.8 Hz, 2.2 Hz, 1H), 4.03 (d, J=12.0 Hz, 1H), 3.96 (s, 3H), 3.81-3.76 (m, 1H), 2.58-2.54 (m, 1H), 2.19-2.16 (m, 2H), 1.83-1.72 (m, 3H). LCMS: 356 (M+1).

Step 3: Preparation of methyl 3-fluoro-4-(1H-pyrazolo[4,3-b]pyridin-3-yl)benzoate (i-1)

A mixture of methyl 3-fluoro-4-(1-(tetrahydro-2H-pyran-2-yl)-1H-pyrazolo[4,3-b]pyridin-3-yl)benzoate i-1b (313 mg, 0.881 mmol) in HCl/EtOAc (~4 M, 4.0 mL) was stirred at room temperature for 1 h. The mixture was diluted with sat. $NaHCO_3$, and extracted with EtOAc. The combined organics were washed with brine, dried over $Na_2SO_4$, and concentrated under reduced pressure to afford the title compound as a solid. $^1H$ NMR (400 MHz, DMSO-$d_6$) δ 13.78 (s, 1H), 8.62-8.55 (m, 2H), 8.10 (d, J=8.4 Hz, 1H), 7.93 (d, J=7.2 Hz, 1H), 7.82 (d, J=10.8 Hz, 1H), 7.46-7.43 (m, 1H), 3.87 (s, 3H).

Intermediate i-2

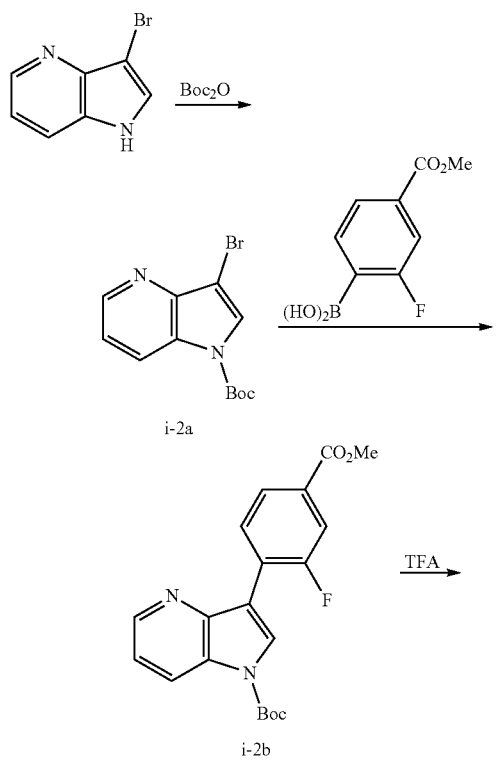

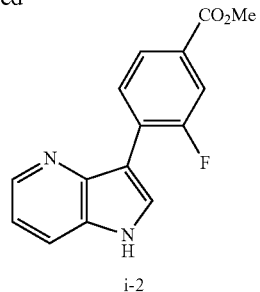

methyl 3-fluoro-4-(1H-pyrrolo[3,2-b]pyridin-3-yl)benzoate

Step 1: Preparation of tert-butyl 3-bromo-1H-pyrrolo[3,2-b]pyridine-1-carboxylate (i-2a)

To a solution of 3-bromo-1H-pyrrolo[3,2-b]pyridine (0.99 g, 5.0 mmol) in dioxane (25 mL) at room temperature were added $BOC_2O$ (1.28 mL, 5.5 mmol) and DMAP (0.061 g, 0.50 mmol). The resulting mixture was stirred at room temperature for 14 h, diluted with $H_2O$, and extracted with EtOAc. The combined organics were washed with brine, dried over $MgSO_4$, filtered, and concentrated. The crude residue was purified by flash chromatography (0-25% EtOAc/hexanes) to give the desired product as a solid. LCMS: 299 (M+1).

Step 2: Preparation of tert-butyl 3-(2-fluoro-4-(methoxycarbonyl)phenyl)-1H-pyrrolo [3,2-b]pyridine-1-carboxylate (i-2b)

To a microwave reaction vial were added tert-butyl 3-bromo-1H-pyrrolo[3,2-b]pyridine-1-carboxylate i-2a (500 mg, 1.68 mmol), 2-fluoro-4-methoxycarbonylphenyl boronic acid (666 mg, 3.37 mmol), $K_3PO_4$ (1.07 g, 5.05 mmol), and dioxane (8.4 mL). The mixture was degassed for 5 min by bubbling argon, followed by the addition of $PdCl_2$(dppf) (123 mg, 0.168 mmol). The vial was sealed and heated at 80° C. for 3 h. The reaction mixture was cooled down, filtered through celite, rinsed with THF. The filtrate was concentrated, and purified by flash chromatography (0-50% EtOAc/hexanes) to give the desired product. LCMS: 371 (M+1).

Step 3: Preparation of methyl 3-fluoro-4-(1H-pyrrolo[3,2-b]pyridin-3-yl)benzoate (i-2)

To a solution of tert-butyl 3-(2-fluoro-4-(methoxycarbonyl)phenyl)-1H-pyrrolo[3,2-b]pyridine-1-carboxylate i-2b (300 mg, 0.81 mmol) in DCM (2 mL) was added TFA (0.5 mL). The reaction mixture was stirred at rt for 3 h, diluted with sat $NaHCO_3$, and extracted with EtOAc. The combined organics were washed with brine, dried over $MgSO_4$, and concentrated. The residue was used directly without further purification. LCMS: 271 (M+1).

Intermediate i-3

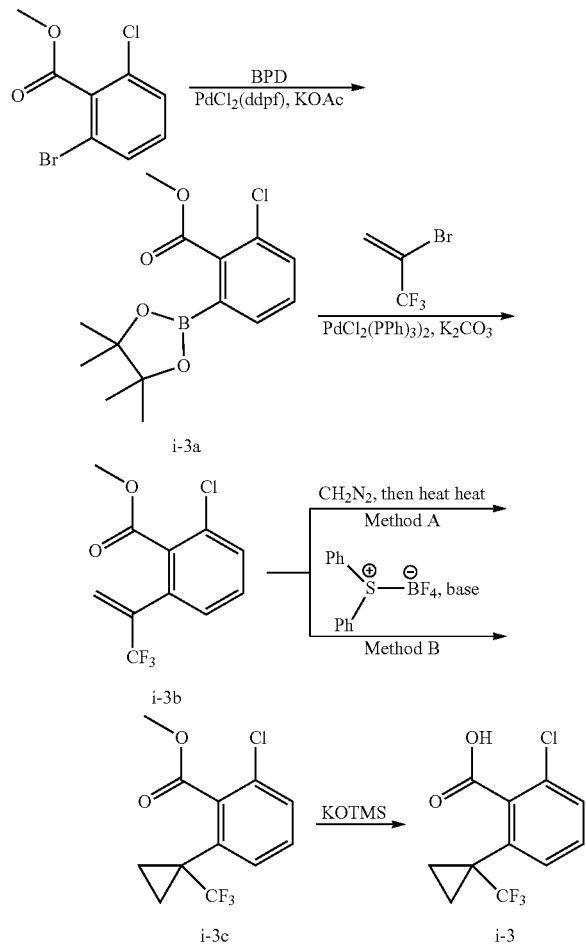

i-3a i-3b i-3c i-3

2-chloro-6-(1-(trifluoromethyl)cyclopropyl)benzoic acid

Step 1. Preparation of methyl 2-chloro-6-(4,4,5,5-tetramethyl-1,3,2-dioxaborolan-2-yl) benzoate (i-3a)

To a solution of methyl 2-bromo-6-chlorobenzoate (7.50 g, 30.1 mmol) in dioxane (65 mL) were added bis(pinacolato)diboron (15.3 g, 60.3 mmol), AcOK (3.54 g, 36.1 mmol), and PdCl$_2$(dppf) (0.66 g, 0.90 mmol). The resulting mixture was stirred at 100° C. for 18 h, cooled down, filtered through celite, and concentrated. The residue was purified by chromatography (0-3% EtOAc in petroleum ether) to give the title compound. $^1$H NMR (400 MHz, CDCl$_3$) δ 7.67 (d, J=7.4 Hz, 1H), 7.46 (d, J=7.8 Hz, 1H), 7.29-7.39 (m, 1H), 3.92 (s, 3H), 1.32 (s, 12H). LCMS: 297 (M+1).

Step 2. Preparation of methyl 2-chloro-6-(3,3,3-trifluoroprop-1-en-2-yl)benzoate (i-3b)

To a solution of methyl 2-chloro-6-(4,4,5,5-tetramethyl-1,3,2-dioxaborolan-2-yl) benzoate i-3a (2.00 g, 6.74 mmol) in THF (25 mL) and H$_2$O (2 mL) were added 2-bromo-3,3,3-trifluoroprop-1-ene (3.54 g, 20.2 mmol), K$_2$CO$_3$ (1.86 g, 13.5 mmol), and bis(triphenylphosphine)palladium(ii) dichloride (120 mg, 0.17 mmol). The resulting mixture was stirred at 70° C. for 5 h, cooled down, and concentrated. The crude residue was purified by chromatography (0-5% EtOAc/hexanes) to give the title compound. $^1$H NMR (400 MHz, CDCl$_3$) δ 7.43-7.49 (m, 1H), 7.37 (t, J=7.8 Hz, 1H), 7.27-7.32 (m, 1H), 6.08 (s, 1H), 5.66 (s, 1H), 3.86 (s, 3H).

Step 3. Preparation of methyl 2-chloro-6-(1-(trifluoromethyl) cyclopropyl)benzoate (i-3c)

Method A: A solution of diazomethane in Et$_2$O (~0.25M, 300 mL) was added to a solution of methyl 2-chloro-6-(3,3,3-trifluoroprop-1-en-2-yl)benzoate i-3b (1.03 g, 3.89 mmol) in DCM (10 mL). The resultant mixture was stirred at 0° C. for 24 h. The reaction was quenched with AcOH (1 mL), concentrated, and purified by column chromatography on silica (0-10% EtOAc/hexanes) to give the resulting cycloaddition intermediate 2-chloro-6-(3-(trifluoromethyl)-4,5-dihydro-3H-pyrazol-3-yl)benzoate. This intermediate was taken up in xylene (5.0 mL) and heated at 130° C. for 6 h. The reaction mixture was cooled down and purified by flash chromatography (0-10% EtOAc/hexanes) to give the title compound.

Method B: To a mixture of methyl 2-chloro-6-(3,3,3-trifluoroprop-1-en-2-yl)benzoate i-3b (0.21 g, 0.79 mmol) and diphenyl(methyl)sulfonium tetrafluoroborate (0.34 g, 1.19 mmol) in THF (3 mL) at −78° C. was added LiHMDS (2.38 mL, 1.0 M in THF, 2.38 mmol) dropwise. The reaction mixture was kept stirring until all of the solid material disappeared. Then the reaction mixture was allowed to warm up slowly to rt, quenched with aq.NH$_4$Cl (15 mL) and extracted with EtOAc. The combined organics were washed with brine, dried over MgSO$_4$, and concentrated. The residue was purified by flash chromatography (0-8%/EtOAc/hexanes) to give the desired product. $^1$H NMR (400 MHz, CDCl$_3$) δ 7.45 (d, J=7.8 Hz, 1H), 7.38-7.43 (m, 1H), 7.35 (d, J=7.8 Hz, 1H), 3.95 (s, 3H), 1.33-1.40 (m, 2H), 1.11-1.19 (m, 2H).

Step 4. Preparation of 2-chloro-6-(1-(trifluoromethyl)cyclopropyl)benzoic acid (i-3)

To a solution of methyl 2-chloro-6-(1-(trifluoromethyl) cyclopropyl) benzoate (0.9 g, 1.6 mmol) i-3c in dioxane (8.0 mL) was added potassium trimethylsilanolate (1.24 g, 9.7 mmol). The resulting mixture was heated at 90° C. for 4 h. The mixture was cooled down, diluted with H$_2$O, and extracted with Et$_2$O (to remove non-polar impurity). The resulting aqueous layer was collected and acidifed with 2N HCl, extracted with EtOAc. The combined organics were washed with brine, dried over MgSO$_4$, and concentrated to give the desired product. $^1$H NMR (400 MHz, CDCl$_3$) δ 7.36-7.48 (m, 2H), 7.28-7.36 (m, 1H), 1.32-1.41 (m, 2H), 1.15-1.19 (m, 2H).

Intermediate i-4

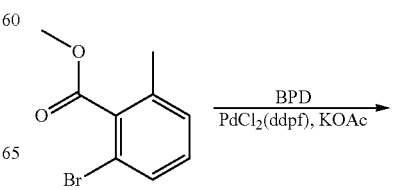

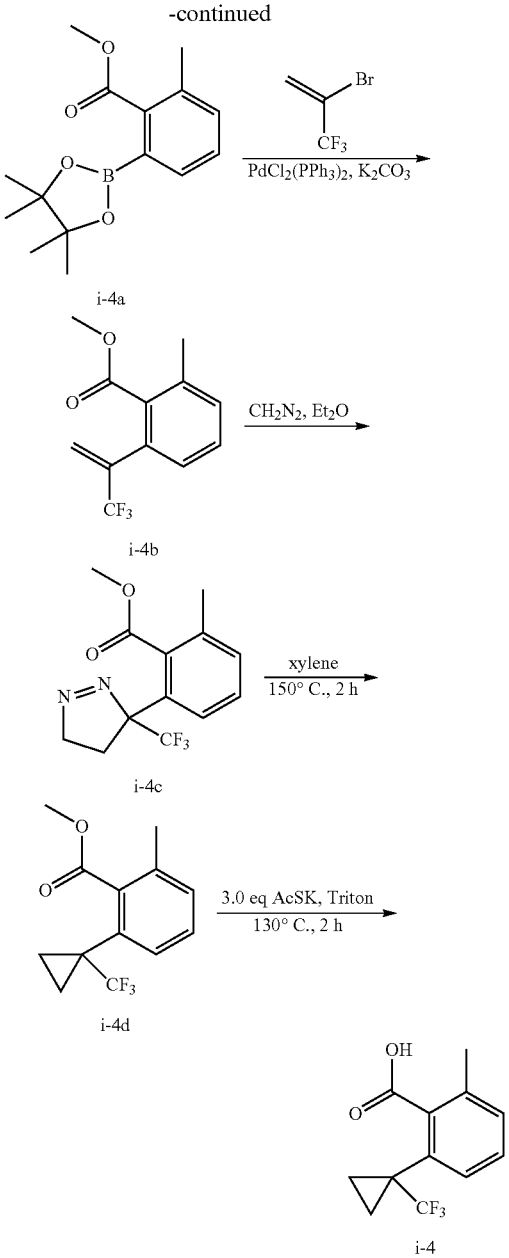

2-methyl-6-(1-(trifluoromethyl)cyclopropyl)benzoic acid (i-4)

Step 1: Preparation of methyl 2-methyl-6-(4,4,5,5-tetramethyl-1,3,2-dioxaborolan-2-yl)benzoate (i-4a)

A mixture of methyl 2-bromo-6-methylbenzoate (4.00 g, 17.46 mmol), 4,4,4',4',5,5,5',5'-octamethyl-2,2'-bi(1,3,2-dioxaborolane) (4.88 g, 19.21 mmol), potassium acetate (5.14 g, 52.4 mmol) and [1,1'-bis(diphenylphosphino) ferrocene]dichloropalladium(ii) (0.77 g, 1.05 mmol) in dioxane (50 mL) was stirred at 100° C. for 18 h. The mixture was cooled down, diluted with EtOAc, filtered, and rinsed with EtOAc. The filtrate was concentrated and the residue was purified by flash chromatography (0-10% EtOAc/hexanes) to give the title compound. $^1$H NMR (400 MHz, CDCl$_3$) δ 7.52 (d, J=7.0 Hz, 1H), 7.27-7.32 (m, 1H), 7.22-7.26 (m, 1H), 3.87 (s, 3H), 2.37 (s, 3H), 1.31 (s, 12H).

Step 2: Preparation of methyl 2-methyl-6-(3,3,3-trifluoroprop-1-en-2-yl)benzoate (i-4b)

A mixture of methyl 2-methyl-6-(4,4,5,5-tetramethyl-1,3,2-dioxaborolan-2-yl) benzoate i-4a (1.80 g, 6.52 mmol), 2-bromo-3,3,3-trifluoroprop-1-ene (2.28 g, 13.03 mmol), K$_2$CO$_3$ (2.70 g, 19.56 mmol), and [1,1'-bis(diphenylphosphino) ferrocene]dichloropalladium(ii) (0.47 g, 0.64 mmol) in dioxane (15 mL) and water (5 mL) was stirred at 95° C. for 16 h. The mixture was cooled, diluted with EtOAc, filtered, and rinsed with EtOAc. The filtrate was concentrated and the residue was purified by flash column chromatography (0-10% EtOAc/hexanes) to give the title compound. $^1$H NMR (400 MHz, CDCl$_3$) δ 7.29-7.35 (m, 1H), 7.24-7.27 (m, 1H), 7.20 (d, J=7.4 Hz, 1H), 6.01 (s, 1H), 5.56 (s, 1H), 3.82 (s, 3H), 2.38 (s, 3H).

Step 3: Preparation of methyl 2-methyl-6-(3-(trifluoromethyl)-4,5-dihydro-3H-pyrazol-3-yl)benzoate (i-4c)

Aqueous KOH (5.50 g, 98 mmol in 10 mL water) was added in portions to a mixture of 1-methyl-1-nitrosourea (2.00 g, 19.40 mmol) in Et$_2$O (10 mL) at 0° C. with careful shaking. The resulting yellow Et$_2$O phase was carefully poured into the stirred solution of methyl 2-methyl-6-(3,3,3-trifluoroprop-1-en-2-yl)benzoate i-4b (1.20 g, 4.91 mmol) in DCM (5 mL) at 0° C. After stirring for 2 h, the reaction mixture was warmed up and stirred at room temperature for 16 h. AcOH (0.2 mL) was added and the mixture was stirred for 10 min, and then concentrated. The residue was purified by flash chromatography (0-40% EtOAc/hexanes) to give the title compound. $^1$H NMR (400 MHz, CDCl$_3$) δ 7.46 (d, J=7.8 Hz, 1H), 7.36 (t, J=7.8 Hz, 1H), 7.27 (d, J=5.9 Hz, 1H), 4.79-4.87 (m, 1H), 4.55-4.65 (m, 1H), 3.90 (s, 3H), 2.40-2.47 (m, 1H), 2.31 (s, 3H), 1.94-2.07 (m, 1H).

Step 4: Preparation of methyl 2-methyl-6-(1-(trifluoromethyl)cyclopropyl)benzoate (i-4d)

A mixture of methyl 2-methyl-6-(3-(trifluoromethyl)-4,5-dihydro-3H-pyrazol-3-yl) benzoate i-4c (386 mg, 1.35 mmol) in xylene (10 mL) was stirred at 150° C. for 2 h. The mixture was cooled down and concentrated to give the title compound. $^1$H NMR (400 MHz, CDCl$_3$) δ 7.34-7.40 (m, 1H), 7.26-7.31 (m, 1H), 7.20 (d, J=7.4 Hz, 1H), 3.87-3.96 (m, 3H), 2.31 (s, 3H), 1.31-1.37 (m, 2H), 1.12 (brs, 2H).

Step 5: Preparation of 2-methyl-6-(1-(trifluoromethyl)cyclopropyl)benzoic acid (i-4)

A mixture of methyl 2-methyl-6-(1-(trifluoromethyl)cyclopropyl)benzoate i-4d (350 mg, 1.36 mmol), potassium thioacetate (464 mg, 4.07 mmol) and Triton(r) X-114 (68 μL, 0.135 mmol) in DMF (5 mL) was stirred at 130° C. for 2 h. The mixture was concentrated and purified by reversed-phase HPLC (CH$_3$CN/H$_2$O, 0.1% TFA) to give the title compound. $^1$H NMR (400 MHz, CDCl$_3$) δ 7.36-7.42 (m, 1H), 7.32 (t, J=7.8 Hz, 1H), 7.20-7.25 (m, 1H), 2.43 (s, 3H), 1.34-1.43 (m, 2H), 1.20 (brs, 2H).

Intermediate i-5

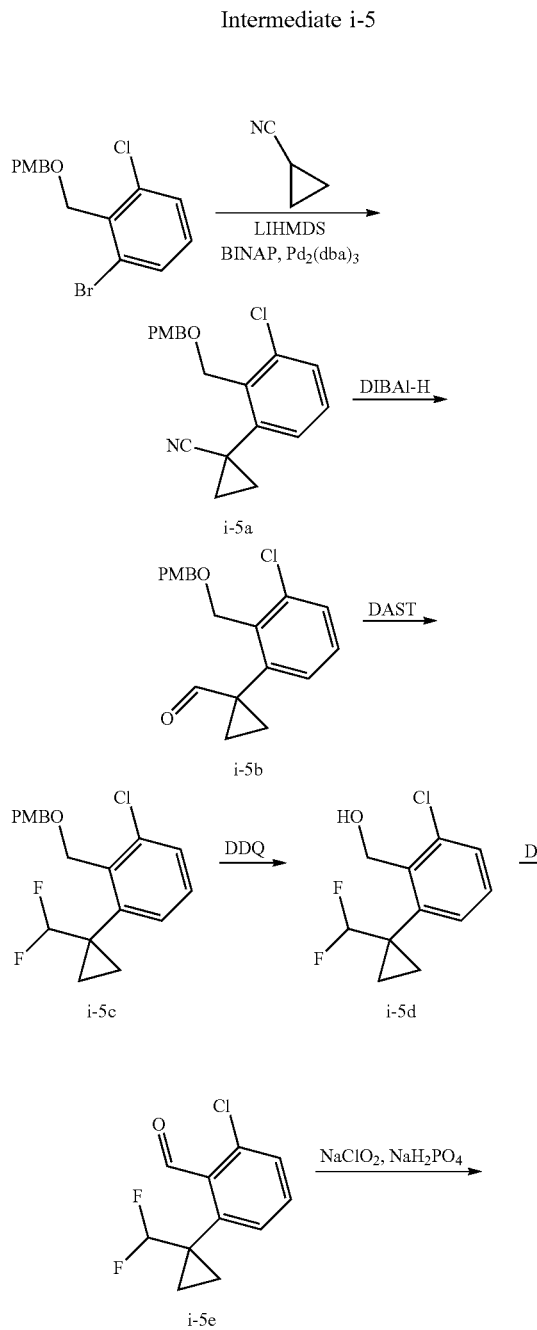

2-chloro-6-(1-(difluoromethyl)cyclopropyl)benzoic acid (i-5)

Step 1: Preparation of 1-(3-chloro-2-(((4-methoxybenzyl)oxy)methyl)phenyl) cyclopropanecarbonitrile (i-5a)

BINAP (1.09 g, 1.75 mmol) and Pd$_2$(dba)$_3$ (670 mg, 0.73 mmol) was dissolved in THF (40 mL). The mixture was stirred at room temperature for 10 min under N$_2$. To the resulting mixture were added 1-bromo-3-chloro-2-(((4-methoxybenzyl)oxy)methyl)-benzene (5 g, 14.6 mmol) and cyclopropanecarbonitrile (1.47 g, 21.9 mmol), followed by LiHMDS (22 mL, 22 mmol) (1.0 Min THF). The mixture was stirred at 80° C. for 18 h under N$_2$, cooled, quenched with sat.NH$_4$Cl, and extracted with EtOAc. The combined organics were washed with brine, dried over Na$_2$SO$_4$, and concentrated. The crude residue was purified by flash chromatography (5-10% EtOAc/hexanes) to give the title compound. $^1$H NMR (400 MHz, CDCl$_3$) δ 7.46 (d, J=7.2 Hz, 2H), 7.33-7.42 (m, 4H), 7.18-7.28 (m, 3H), 6.92 (d, J=8.4 Hz, 2H), 4.86 (s, 2H), 4.64 (s, 2H), 3.78-3.88 (m, 3H), 1.37-1.46 (m, 2H), 1.21-1.27 (m, 2H).

Step 2: Preparation of 1-(3-chloro-2-(((4-methoxybenzyl)oxy)methyl) phenyl)cyclopropanecarbaldehyde (i-5b)

To a solution of 1-(3-chloro-2-(((4-methoxybenzyl)oxy) methyl)phenyl)cyclo propane carbonitrile i-5a (2.0 g, 6.10 mmol) in toluene (30 mL) was added DIBAL-H (12.2 mL, 12.2 mmol) (1.0M) at −78° C. The mixture was allowed to warm to 0° C. for 5 h, and then cooled back to −78° C. Isopropyl alcohol (0.5 mL) was carefully added dropwise. After stirring for 30 min, the reaction mixture was warmed to 0° C. The reaction mixture was diluted with water and extracted with EtOAc. The combined organic layers were washed with brine, dried over Na$_2$SO$_4$, and concentrated. The residue was purified by silica gel column chromatography (0-20% EtOAc/hexanes) to give the title compound. $^1$H NMR (400 MHz, CDCl$_3$) δ 9.17 (s, 1H), 7.37-7.44 (m, 1H), 7.30 (d, J=8.4 Hz, 2H), 7.17-7.27 (m, 2H), 6.89 (d, J=8.6 Hz, 2H), 4.61 (s, 2H), 4.52 (s, 2H), 3.71-3.89 (m, 3H), 1.53-1.58 (m, 2H), 1.39-1.46 (m, 2H).

Step 3: Preparation of 1-chloro-3-(1-(difluoromethyl)cyclopropyl)-2-(((4-methoxy benzyl)oxy)methyl)benzene (i-5c)

To a solution of 1-(3-chloro-2-(((4-methoxybenzyl)oxy) methyl)phenyl) cyclopropanecarbaldehyde (1 g, 3.02 mmol) i-5b in DCM (8 mL) was added DAST (0.80 mL, 6.1 mmol) at 0° C. The mixture was stirred at 0° C. for 1 h and then at room temperature for 3 h. The mixture was quenched with saturated NaHCO$_3$ and extracted with DCM. The combined organic layers were washed with brine, dried over Na$_2$SO$_4$, and concentrated. The crude residue was purified by flash chromatography (3-10% EtOAc/hexanes) to afford the title compound. $^1$H NMR (400 MHz, CDCl$_3$) δ 7.29-7.39 (m, 4H), 7.19-7.24 (m, 1H), 6.85-6.95 (m, 2H), 5.60-5.89 (m, 1H), 4.76 (s, 2H), 4.61 (s, 2H), 3.82 (s, 3H), 1.17 (s, 2H), 1.04 (brs, 2H).

Step 4: Preparation of (2-chloro-6-(1-(difluoromethyl)cyclopropyl)phenyl) methanol (i-5d)

To a solution of 1-chloro-3-(1-(difluoromethyl) cyclopropyl)-2-(((4-methoxy benzyl) oxy)methyl)benzene i-5c (100 mg, 0.283 mmol) in DCM (3 mL) and H₂O (0.5 mL) was added DDQ (129 mg, 0.57 mmol). The mixture was stirred at room temperature for 2 h, diluted with DCM, filtered through celite. The filtrate was washed with H₂O and brine. The organic layer was separated, dried over Na$_2$SO$_4$, concentrated. The residue was taken up in MeOH (4 mL), followed by the addition of NaBH$_4$ (21 mg, 0.567 mmol) at 0° C. After the mixture was stirred for 1 h, H₂O (0.5 mL) was added. The mixture was concentrated, and the residue was purified by flash chromatography (0-5% EtOAc/hexanes) to afford the title compound. $^1$H NMR (400 MHz, CDCl$_3$) δ 7.38 (dd, J=14.2 Hz, 7.7 Hz, 2H), 7.22-7.26 (m, 1H), 5.51-5.89 (m, 1H), 5.00 (s, 2H), 2.16 (d, J=14.7 Hz, 1H), 1.30 (s, 2H), 1.09 (brs, 2H).

Step 5: Preparation of 2-chloro-6-(1-(difluoromethyl)cyclopropyl)benzaldehyde (i-5e)

To a solution of 2-chloro-6-(1-(difluoromethyl)cyclopropyl)phenyl) methanol i-5d (70 mg, 0.30 mmol) in DCM (3 mL) was added DMP (255 mg, 0.60 mmol) at 0° C. The reaction was stirred at 0° C. for 2 h. The mixture was diluted with DCM, filtered and concentrated. The residue was purified by prep-TLC (10% EtOAc/hexanes) to give the title compound. $^1$H NMR (400 MHz, CDCl$_3$) δ 10.61 (s, 1H), 7.36-7.57 (m, 3H), 5.97-6.28 (m, 1H), 1.35-1.39 (m, 2H), 0.80 (brs, 2H).

Step 6: Preparation of 2-chloro-6-(1-(difluoromethyl)cyclopropyl)benzoic acid (i-5)

2-methylbut-2-ene (182 mg, 2.60 mmol) was added to a stirred mixture of 2-chloro-6-(1-(difluoromethyl)cyclopropyl)benzaldehyde i-5e (60 mg, 0.260 mmol) in t-BuOH (4 mL) at 0° C. Then a solution of sodium chlorite (31 mg, 0.343 mmol) in water (1 mL) was added, followed by the addition of a solution of sodium dihydrogen phosphate (62 mg, 0.52 mmol) in H₂O (1 mL). The reaction was stirred at 0° C. for 2 h, and then at room temperature for 17 h. The mixture was acidified with HCl (1.0M) and extracted with EtOAc. The combined organics were washed with brine, dried over Na$_2$SO$_4$, and concentrated to give the title compound. $^1$H NMR (400 MHz, CDCl$_3$) δ 7.46-7.34 (m, 3H), 6.32-5.96 (m, 1H), 1.30-1.27 (m, 2H), 1.02-0.98 (m, 2H).

Intermediate i-6

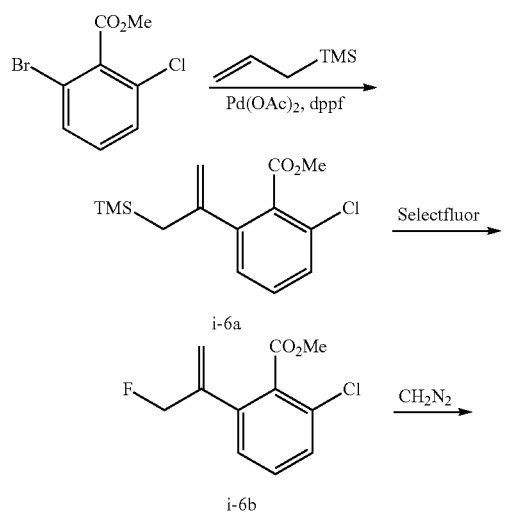

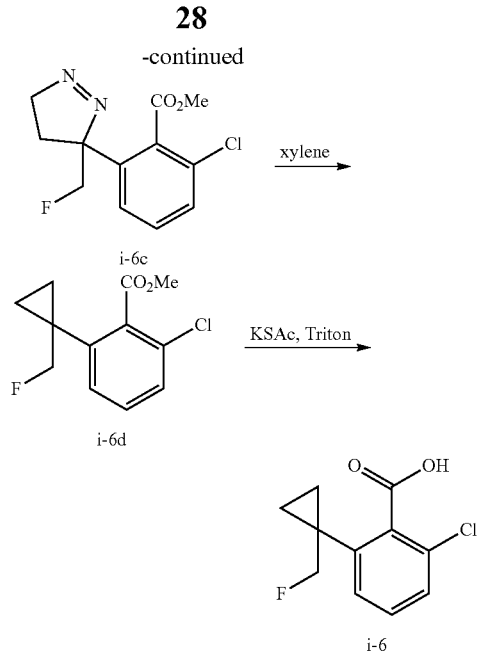

2-chloro-6-(1-(fluoromethyl)cyclopropyl)benzoic acid (i-6)

Step 1: Preparation of methyl-2-chloro-6-(3-(trimethylsilyl)prop-1-en-2-yl)benzoate (i-6a)

To a mixture of methyl-2-bromo-6-chlorobenzoate (4.60 g, 18.4 mmol), TEA (7.7 mL, 55 mmol) and allyltrimethylsilane (2.74 g, 24.0 mmol) in toluene (150 mL) were added Pd(OAc)$_2$ (0.21 g, 0.92 mmol) and dppf (1.02 g, 1.84 mmol). The mixture was stirred at 130° C. for 18 h under N$_2$ atmosphere. Additional reagents, including allyltrimethylsilane (2.74 g, 24.0 mmol), TEA (7.7 mL, 55 mmol), Pd(OAc)$_2$ (0.21 g, 0.92 mmol) and dppf (1.02 g, 1.84 mmol), were added and the mixture was stirred for another 18 h. This operation was repeated one more time. The mixture was cooled, diluted with H₂O and extracted with EtOAc. The organic layers were concentrated and purified by flash chromatography (100% hexanes) to give the title compound. $^1$H NMR (400 MHz, CDCl$_3$) δ 7.30 (brs, 1H), 7.22 (s, 1H), 7.13 (d, J=3.5 Hz, 1H), 4.97 (d, J=7.8 Hz, 2H), 3.89 (s, 3H), 1.90 (s, 2H), −0.07 (s, 9H).

Step 2: Preparation of methyl-2-chloro-6-(3-fluoroprop-1-en-2-yl)benzoate (i-6b)

To a solution of methyl-2-chloro-6-(3-(trimethylsilyl)prop-1-en-2-yl) benzoate i-6a (4.50 g, 15.9 mmol) in MeCN (100 mL) was added Select-fluor (14.1 g, 39.8 mmol). The mixture was stirred at room temperature for 24 h and concentrated in vacuo. The residue was purified by flash column chromatography (100% hexanes) to give the title compound. LCMS 229 (M+1). $^1$H NMR (400 MHz, CDCl$_3$) δ 7.31-7.43 (m, 2H), 7.20 (d, J=7.4 Hz, 1H), 5.52 (s, 1H), 5.29 (s, 1H), 5.09 (s, 1H), 4.98 (s, 1H), 3.81-3.92 (m, 3H).

Step 3: Preparation of methyl-2-chloro-6-(3-(fluoromethyl)-4,5-dihydro-3H-pyrazol-3-yl) benzoate (i-6c)

To a solution of methyl-2-chloro-6-(3-fluoroprop-1-en-2-yl)benzoate i-6b (1.00 g, 4.37 mmol) in Et$_2$O (10 mL) was added diazomethane (43.7 mL, 21.9 mmol, ~0.5 M in Et$_2$O) at 0° C. The mixture was stirred at room temperature for 18 h. Then the reaction mixture was concentrated and purified by flash chromatography (0-20% EtOAc/hexanes) to give the title compound. LCMS: 271 (M+1).

Step 4: Preparation of methyl-2-chloro-6-(1-(fluoromethyl)cyclopropyl)benzoate (i-6d)

A solution of methyl-2-chloro-6-(3-(fluoromethyl)-4,5-dihydro-3H-pyrazol-3-yl)benzoate i-6c (700 mg, 2.59 mmol) in xylene (50 mL) was stirred at 150° C. for 18 h. The mixture was cooled down and concentrated in vacuo. The residue was purified by Prep-TLC (5% EtOAc/hexanes) to give the title compound. $^1$H NMR (400 MHz, CDCl$_3$) δ 7.39 (d, J=6.6 Hz, 1H), 7.29-7.36 (m, 2H), 4.45 (s, 1H), 4.33 (s, 1H), 3.95 (s, 3H), 0.95 (s, 4H). LCMS: 243 (M+1),

Step 5: Preparation of 2-chloro-6-(1-(fluoromethyl)cyclopropyl)benzoic acid (i-6)

To a solution of methyl-2-chloro-6-(1-(fluoromethyl)cyclopropyl) benzoate i-6d (600 mg, 2.47 mmol) in DMF (15 mL) was added potassium thioacetate (847 mg, 7.42 mmol), followed by the addition of polyethylene glycol tert-octylphenyl ether (Triton) (127 mg, 0.247 mmol). The resulting mixture was heated at 130° C. for 1 h. The mixture was cooled down, diluted with H$_2$O, and acidified with 1M HCl and extracted with EtOAc. The combined organic layers were concentrated and purified by Prep-HPLC to give the title compound. $^1$H NMR (400 MHz, CDCl$_3$) δ 9.75-9.98 (m, 1H), 7.41-7.48 (m, 1H), 7.31-7.40 (m, 2H), 4.50 (s, 1H), 4.38 (s, 1H), 0.98-1.10 (m, 4H).

Intermediate i-7

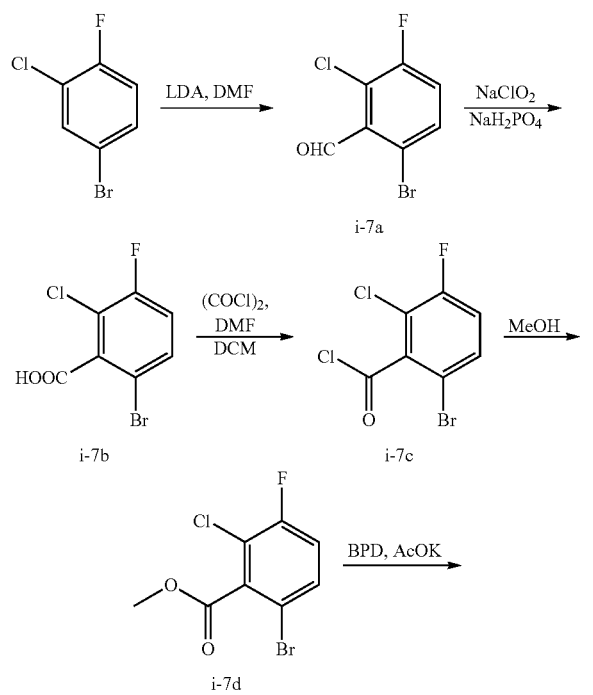

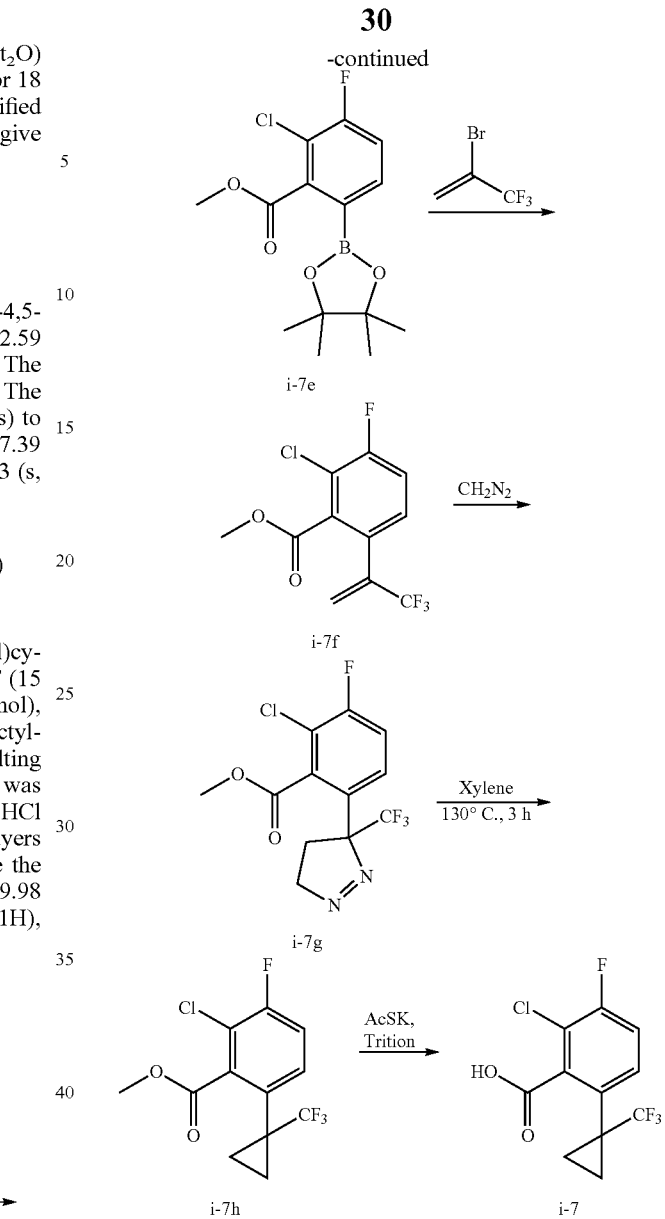

2-chloro-3-fluoro-6-(1-(trifluoromethyl)cyclopropyl) benzoic acid (i-7)

Step 1: Preparation of 6-bromo-2-chloro-3-fluorobenzaldehyde (i-7a)

To a solution of 4-bromo-2-chloro-1-fluorobenzene (20 g, 95 mmol) in THF (150 mL) was added lithium diisopropylamide (55 mL, 2.0 M in THF, 110 mmol) dropwise at −78° C. The resulting mixture was stirred at −78° C. for 2 h. Then DMF (11 mL, 142 mmol) was added and the reaction mixture was stirred at −78° C. for additional 2 h. The reaction was quenched with sat. NH$_4$Cl, and extracted with EtOAc. The combined organics were washed with brine, dried over Na$_2$SO$_4$, and concentrated. The crude residue was purified by flash chromatography to give the title compound. $^1$H NMR (400 MHz, DMSO-d$_6$) δ 10.71 (s, 1H), 8.36 (dd, J=8.6 Hz, 4.7 Hz, 1H), 8.18 (t, J=8.8 Hz, 1H).

Step 2: Preparation of 6-bromo-2-chloro-3-fluorobenzoic acid (i-7b)

To a solution of 6-bromo-2-chloro-3-fluorobenzaldehyde i-7a (7 g, 29.5 mmol) and 2-methylbut-2-ene (10.3 g, 147 mmol) in t-BuOH (100 mL) was added a solution of sodium dihydrogen phosphate (7.07 g, 59.0 mmol) in $H_2O$ (20 mL) at 0° C., followed by the addition of sodium chlorite (3.47 g, 38.3 mmol) in $H_2O$ (20 mL) dropwise. The reaction mixture was stirred at room temperature for 18 h. Then the pH was carefully adjusted to about 5-6 with aq. HCl (1 M). The mixture was extracted with EtOAc. The combined organics were dried over $Na_2SO_4$ and concentrated to give the title compound. $^1$H NMR (400 MHz, $CDCl_3$) δ 7.34 (dd, J=8.8 Hz, 4.1 Hz, 1H), 6.93 (t, J=8.6 Hz, 1H).

Step 3: Preparation of 6-bromo-2-chloro-3-fluorobenzoyl chloride (i-7c)

To a solution of 6-bromo-2-chloro-3-fluorobenzoic acid i-7b (5 g, 19.7 mmol) in DCM (60 mL) was added $(COCl)_2$ (6 mL, 68.5 mmol), followed by catalytic DMF (0.3 mL, 3.87 mmol). The reaction mixture was stirred at room temperature for 4 h, concentrated and used directly for next step.

Step 4: Preparation of methyl 6-bromo-2-chloro-3-fluorobenzoate (i-7d)

A mixture of 6-bromo-2-chloro-3-fluorobenzoyl chloride i-7c (5.36 g, 19.71 mmol) in MeOH (50 mL) was stirred at 85° C. for 18 h. The mixture was cooled down and concentrated. The residue was purified by flash chromatography to give the title compound. $^1$H NMR (400 MHz, $CDCl_3$) δ 7.48 (dd, J=8.6 Hz, 4.3 Hz, 1H), 7.11 (t, J=8.6 Hz, 1H), 4.01 (s, 3H).

Step 5: Preparation of methyl 2-chloro-3-fluoro-6-(4,4,5,5-tetramethyl-1,3,2-dioxaborolan-2-yl)benzoate (i-7e)

To a solution of methyl 6-bromo-2-chloro-3-fluorobenzoate i-7d (2.7 g, 10.1 mmol) in dioxane (50 mL) were added KOAc (1.29 g, 13.1 mmol), 4,4,4',4',5,5,5',5'-octamethyl-2,2'-bi(1,3,2-dioxaborolane) (5.13 g, 20.2 mmol), and $PdCl_2$(dppf) (0.37 g, 0.51 mmol) under $N_2$.

The reaction mixture was stirred at 80° C. for 18 h. The mixture was filtered and rinsed with EtOAc. The filtrate was concentrated and the residue was purified by flash chromatography to give the title compound as a solid. $^1$H NMR (400 MHz, $CDCl_3$) δ 7.69 (dd, J=8.0 Hz, 5.2 Hz, 1H), 7.19 (t, J=8.4 Hz, 1H), 3.94 (s, 3H), 1.29-1.39 (m, 12H).

Step 6: Preparation of methyl 2-chloro-3-fluoro-6-(3,3,3-trifluoroprop-1-en-2-yl)benzoate (i-7f)

To a solution of methyl 2-chloro-3-fluoro-6-(4,4,5,5-tetramethyl-1,3,2-dioxaborolan-2-yl)benzoate i-7e (4 g, 6.4 mmol) in dioxane (20 mL) and $H_2O$ (4 mL) were added $K_2CO_3$ (2 g, 14.5 mmol), 2-bromo-3,3,3-trifluoroprop-1-ene (8 g, 45.7 mmol) and $PdCl_2$(dppf) (0.23 g, 0.32 mmol) under $N_2$. The reaction mixture was stirred at 80° C. for 18 h. The mixture was filtered through celite, rinsed with EtOAc. The filtrate was washed with brine, dried over $Na_2SO_4$, filtered and concentrated. The residue was purified by flash chromatography. $^1$H NMR (400 MHz, DMSO-$d_6$) δ 7.66 (t, J=8.9 Hz, 1H), 7.48 (dd, J=8.6 Hz, 4.6 Hz, 1H), 6.28 (s, 1H), 5.81 (s, 1H), 3.83 (s, 3H).

Step 7: Preparation of methyl 2-chloro-3-fluoro-6-(3-(trifluoromethyl)-4,5-dihydro-3H-pyrazol-3-yl)benzoate (i-7g)

To a solution of methyl 2-chloro-3-fluoro-6-(3,3,3-trifluoroprop-1-en-2-yl) benzoate (800 mg, 2.55 mmol) i-7f in $Et_2O$ (15 mL) was added a solution of diazomethane (60 mL, 30.0 mmol, 0.5M in $Et_2O$) at 0° C. dropwise. The reaction mixture was stirred at 0° C. for 2 h, and then at room temperature for 18 h. The mixture was quenched with AcOH (2 mL), concentrated under reduced pressure. The residue was purified by flash chromatography to give the title compound. $^1$H NMR (400 MHz, $CDCl_3$) δ 7.64 (dd, J=8.7 Hz, 4.5 Hz, 1H), 7.30 (d, J=8.7 Hz, 1H), 4.86-5.01 (m, 1H), 4.57-4.71 (m, 1H), 3.88-4.00 (m, 3H), 2.45 (m, 1H), 1.92-2.02 (m, 1H).

Step 8: Preparation of methyl 2-chloro-3-fluoro-6-(1-(trifluoromethyl)cyclo propyl)benzoate (i-7h)

A solution of methyl 2-chloro-3-fluoro-6-(3-(trifluoromethyl)-4,5-dihydro-3H-pyrazol-3-yl)benzoate i-7g (650 mg, 2.02 mmol) in xylene (20 mL) was stirred at 130° C. for 3 h. The mixture was cooled down and concentrated to give the title compound.

Step 9: Preparation of 2-chloro-3-fluoro-6-(1-(trifluoromethyl)cyclopropyl) benzoic acid (i-7)

To a mixture of methyl 2-chloro-3-fluoro-6-(1-(trifluoromethyl) cyclopropyl)benzoate i-7h (590 mg, 1.989 mmol) in DMF (8 mL) were added potassium ethanethioate (681 mg, 5.97 mmol) and TRITON(R) X-405 (102 mg, 0.199 mmol). The mixture was stirred at 130° C. for 2 h, cooled down and concentrated. The residue was dissolved in $H_2O$ (20 mL), acidified with 1M HCl to PH=5~6, and extracted with EtOAc. The combined organics were washed with brine, dried over $Na_2SO_4$, and concentrated. The residue was purified by preparative HPLC to give the title compound $^1$H NMR (400 MHz, $CDCl_3$) δ 7.49 (dd, J=8.5 Hz, 4.7 Hz, 1H), 7.21-7.26 (m, 1H), 1.43 (t, J=6.0 Hz, 2H), 1.22 (brs, 2H).

Intermediate i-8

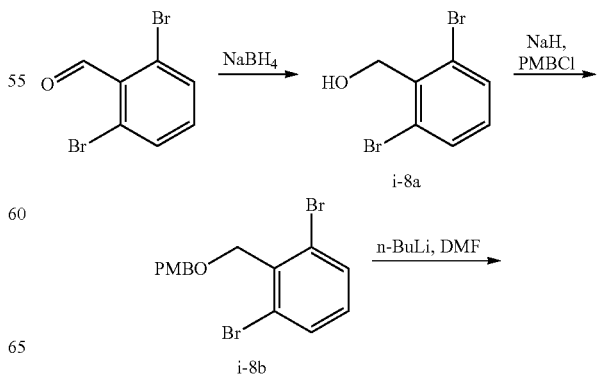

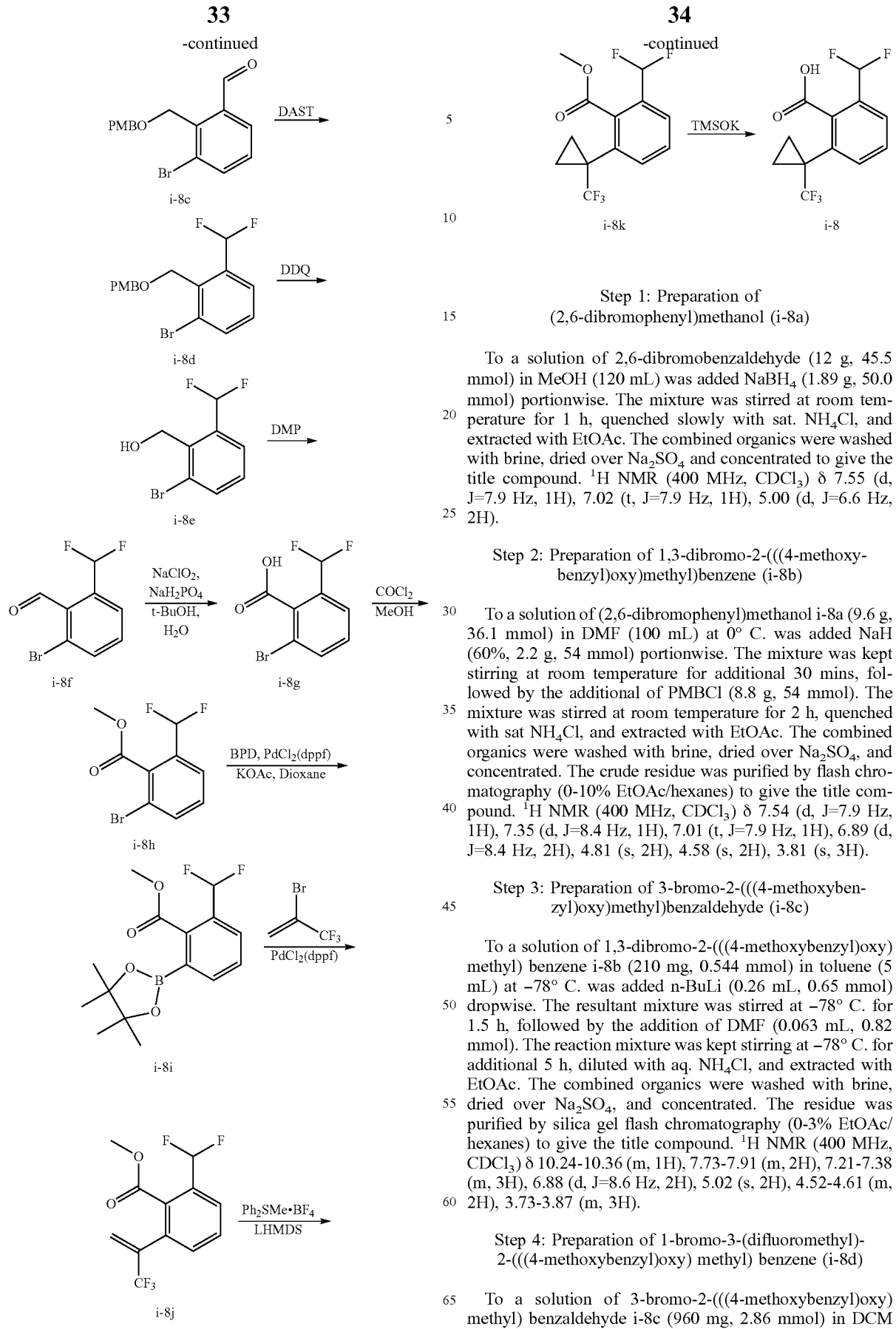

Step 1: Preparation of (2,6-dibromophenyl)methanol (i-8a)

To a solution of 2,6-dibromobenzaldehyde (12 g, 45.5 mmol) in MeOH (120 mL) was added NaBH₄ (1.89 g, 50.0 mmol) portionwise. The mixture was stirred at room temperature for 1 h, quenched slowly with sat. NH₄Cl, and extracted with EtOAc. The combined organics were washed with brine, dried over Na₂SO₄ and concentrated to give the title compound. ¹H NMR (400 MHz, CDCl₃) δ 7.55 (d, J=7.9 Hz, 1H), 7.02 (t, J=7.9 Hz, 1H), 5.00 (d, J=6.6 Hz, 2H).

Step 2: Preparation of 1,3-dibromo-2-(((4-methoxybenzyl)oxy)methyl)benzene (i-8b)

To a solution of (2,6-dibromophenyl)methanol i-8a (9.6 g, 36.1 mmol) in DMF (100 mL) at 0° C. was added NaH (60%, 2.2 g, 54 mmol) portionwise. The mixture was kept stirring at room temperature for additional 30 mins, followed by the additional of PMBCl (8.8 g, 54 mmol). The mixture was stirred at room temperature for 2 h, quenched with sat NH₄Cl, and extracted with EtOAc. The combined organics were washed with brine, dried over Na₂SO₄, and concentrated. The crude residue was purified by flash chromatography (0-10% EtOAc/hexanes) to give the title compound. ¹H NMR (400 MHz, CDCl₃) δ 7.54 (d, J=7.9 Hz, 1H), 7.35 (d, J=8.4 Hz, 1H), 7.01 (t, J=7.9 Hz, 1H), 6.89 (d, J=8.4 Hz, 2H), 4.81 (s, 2H), 4.58 (s, 2H), 3.81 (s, 3H).

Step 3: Preparation of 3-bromo-2-(((4-methoxybenzyl)oxy)methyl)benzaldehyde (i-8c)

To a solution of 1,3-dibromo-2-(((4-methoxybenzyl)oxy) methyl) benzene i-8b (210 mg, 0.544 mmol) in toluene (5 mL) at −78° C. was added n-BuLi (0.26 mL, 0.65 mmol) dropwise. The resultant mixture was stirred at −78° C. for 1.5 h, followed by the addition of DMF (0.063 mL, 0.82 mmol). The reaction mixture was kept stirring at −78° C. for additional 5 h, diluted with aq. NH₄Cl, and extracted with EtOAc. The combined organics were washed with brine, dried over Na₂SO₄, and concentrated. The residue was purified by silica gel flash chromatography (0-3% EtOAc/ hexanes) to give the title compound. ¹H NMR (400 MHz, CDCl₃) δ 10.24-10.36 (m, 1H), 7.73-7.91 (m, 2H), 7.21-7.38 (m, 3H), 6.88 (d, J=8.6 Hz, 2H), 5.02 (s, 2H), 4.52-4.61 (m, 2H), 3.73-3.87 (m, 3H).

Step 4: Preparation of 1-bromo-3-(difluoromethyl)-2-(((4-methoxybenzyl)oxy) methyl) benzene (i-8d)

To a solution of 3-bromo-2-(((4-methoxybenzyl)oxy) methyl) benzaldehyde i-8c (960 mg, 2.86 mmol) in DCM (15 mL) was added DAST (1.135 mL, 8.59 mmol). The resultant mixture was stirred at 40° C. for 3 h. The mixture was cooled down, followed by the addition of MeOH (2 mL). The mixture was concentrated and purified by flash chromatography (0-1% EtOAc/hexanes), to give the title compound. $^1$H NMR (400 MHz, CDCl$_3$) δ 7.67 (d, J=7.9 Hz, 1H), 7.60 (d, J=7.7 Hz, 1H), 7.22-7.25 (m, 3H), 6.85-7.12 (m, 1H), 6.88 (d, J=8.4 Hz, 2H), 4.78 (s, 2H), 4.51 (s, 2H), 3.79 (s, 3H).

Step 5: Preparation of (2-bromo-6-(difluoromethyl)phenyl)methanol (i-8e)

To a solution of 1-bromo-3-(difluoromethyl)-2-(((4-methoxy benzyl) oxy) methyl)benzene i-8d (1.60 g, 4.48 mmol) in DCM (20 mL) at room temperature was added DDQ (1.22 g, 5.38 mmol). The reaction mixture was kept stirring at room temperature for 2 h, quenched with sat. Na$_2$SO$_3$ and extracted with EtOAc. The combined organics were washed with brine, dried over Na$_2$SO$_4$ and concentrated to afford the title compound. $^1$H NMR (400 MHz, CDCl$_3$) δ 7.71 (d, J=7.9 Hz, 1H), 7.56 (d, J=7.7 Hz, 1H), 7.25-7.30 (m, 1H), 4.93 (d, J=5.1 Hz, 2H), 2.01 (d, J=5.5 Hz, 1H).

Step 6: Preparation of 2-bromo-6-(difluoromethyl)benzaldehyde (i-8f)

To a solution of (2-bromo-6-(difluoromethyl)phenyl) methanol i-8e (780 mg, 3.29 mmol) in DCM (15 mL) was added DMP (1.68 g, 3.95 mmol). The resultant mixture was stirred at room temperature for 2 h, diluted with sat. NaHCO$_3$, and extracted with DCM. The combined organics were washed with brine, dried over Na$_2$SO$_4$ and concentrated. The residue was purified by flash chromatography (0-10% EtOAc/hexanes) to give the title compound. $^1$H NMR (400 MHz, CDCl$_3$) δ 10.50 (s, 1H), 7.82 (t, J=7.6 Hz, 2H), 7.27-7.58 (m, 2H).

Step 7: Preparation of 2-bromo-6-(difluoromethyl)benzoic acid (i-8g)

A solution of sodium dihydrogen phosphate (1.48 g, 12.3 mmol) and sodium chlorite (446 mg, 4.94 mmol) in H$_2$O (6.0 mL) were added to a solution of 2-bromo-6-(difluoromethyl)benzaldehyde i-8f (580 mg, 2.47 mmol) and 2-methylbut-2-ene (3.46 g, 49.4 mmol) in t-BuOH (15 mL). The resultant mixture was stirred at room temperature for 2.5 h, quenched with sat. Na$_2$SO$_3$, and extracted with hexanes. The aqueous layer was separated, acidified with aq. HCl, and extracted with EtOAc. The combined organics were washed with brine, dried over Na$_2$SO$_4$ and concentrated to give the title compound. $^1$H NMR (400 MHz, CDCl$_3$) δ 7.77 (d, J=7.9 Hz, 1H), 7.65 (d, J=7.9 Hz, 1H), 7.39-7.49 (m, 1H), 6.75-7.11 (m, 1H).

Step 8: Preparation of methyl 2-bromo-6-(difluoromethyl)benzoate (i-8h)

Oxalyl dichloride (1.03 mL, 11.8 mmol) was added to a solution of 2-bromo-6-(difluoromethyl)benzoic acid i-8g (590 mg, 2.35 mmol) and DMF (9.1 µL, 0.118 mmol) in DCM (15 mL). The resultant mixture was stirred at room temperature for 1 h and concentrated. To the resultant residue containing acid chloride was added MeOH (20.0 mL). The mixture was stirred at room temperature for 2h and concentrated to give the title compound.

Step 9: Preparation of methyl 2-(difluoromethyl)-6-(4,4,5,5-tetramethyl-1,3,2-dioxaborolan-2-yl)benzoate (i-8i)

PdCl$_2$(dppf) (84 mg, 0.12 mmol) was added to a mixture of 2-bromo-6-(difluoromethyl)benzoate (i-8h) (609 mg, 2.3 mmol), bis(pinacolato) diboron (1.169 g, 4.60 mmol) and KOAc (271 mg, 2.76 mmol) in dioxane (15 mL). The resultant mixture was stirred at 80° C. for 16 h, cooled down, diluted with H$_2$O and EtOAc. The organic layer was separated, washed with brine, dried over Na$_2$SO$_4$, and concentrated. The residue was purified by silica gel flash chromatography (0-4% EtOAc/hexanes) to give the title compound. $^1$H NMR (400 MHz, CDCl$_3$) δ 7.76 (dd, J=10.9 Hz, 7.8 Hz, 1H), 7.49-7.60 (m, 1H), 6.92-7.23 (m, 1H), 3.90 (s, 3H), 1.34 (s, 12H).

Step 10: Preparation of methyl 2-(difluoromethyl)-6-(3,3,3-trifluoroprop-1-en-2-yl) benzoate To a solution of methyl 2-(difluoromethyl)-6-(4,4,5,5-tetramethyl-1,3,2-dioxaborolan-2-yl)benzoate i-8i (395 mg, 0.861 mmol) in dioxane (10 mL) and H$_2$O (1.0 mL) were added 2-bromo-3,3,3-trifluoroprop-1-ene (602 mg, 3.44 mmol), K$_2$CO$_3$ (238 mg, 1.72 mmol), and PdCl$_2$(dppf) (63 mg, 0.086 mmol). The resultant mixture was stirred at 70° C. for 20 h. The mixture was cooled down, diluted with EtOAc, brine, dried over Na$_2$SO$_4$ and concentrated. The residue was purified by silica gel flash chromatography (0-3% EtOAc/hexanes) to give the title compound. $^1$H NMR (400 MHz, CDCl$_3$) δ 7.75 (d, J=7.7 Hz, 1H), 7.58 (t, J=7.7 Hz, 1H), 7.45-7.52 (m, 1H), 6.78-7.14 (m, 1H), 6.08 (s, 1H), 5.59 (s, 1H), 3.85 (s, 3H).

Step 11: Preparation of methyl 2-(difluoromethyl)-6-(1-(trifluoro methyl)cyclo propyl) benzoate (i-8k)

To a mixture of methyl 2-(difluoromethyl)-6-(3,3,3-trifluoroprop-1-en-2-yl)benzoate i-8j (50 mg, 0.178 mmol), diphenyl(methyl) sulfonium tetrafluoroborate (77 mg, 0.268 mmol) in THF (3 mL) at −78° C. was added LiHMDS (0.625 mL, 0.625 mmol) slowly. The reaction temperature was kept below −60° C. during addition. The reaction was allowed to stir under N$_2$ atmosphere until the entire solid went into solution. Then the reaction mixture was slowly warmed to room temperature and stirred for 12 h. The reaction mixture was diluted with sat. NH$_4$Cl and extracted with EtOAc. The combined organics were washed with brine, dried over Na$_2$SO$_4$, and concentrated. The residue was purified by flash chromatography (0-10% EtOAc/hexanes) to give the title compound. $^1$H NMR (400 MHz, CDCl$_3$) δ 7.67 (d, J=7.7 Hz, 2H), 7.51-7.57 (m, 1H), 6.67-7.04 (m, 1H), 3.95 (s, 3H), 3.85 (s, 1H), 1.39-1.47 (m, 2H), 1.15 (brs, 2H).

Step 12: Preparation of 2-(difluoromethyl)-6-(1-(trifluoromethyl)cyclopropyl) benzoic acid (i-8)

Potassium trimethylsilanolate (65 mg, 0.507 mmol) was added to a stirred mixture of methyl 2-(difluoromethyl)-6-(1-(trifluoromethyl)cyclopropyl) benzoate (50 mg, 0.17 mmol) in 1,4-dioxane (1 mL). The mixture was stirred at 90° C. for 18 h. The mixture was cooled down, diluted with H$_2$O and extracted with hexanes. The resulting aqueous layer was acidified with 2M HCl, extracted with EtOAc. The combined organics were washed with brine, dried over MgSO$_4$, and concentrated to give the title compound. $^1$H NMR (400

MHz, CDCl$_3$) δ 7.72 (d, J=7.7 Hz, 2H), 7.55-7.62 (m, 1H), 6.83-7.17 (m, 1H), 1.48 (s, 2H), 1.26 (brs, 2H).

Intermediate i-9

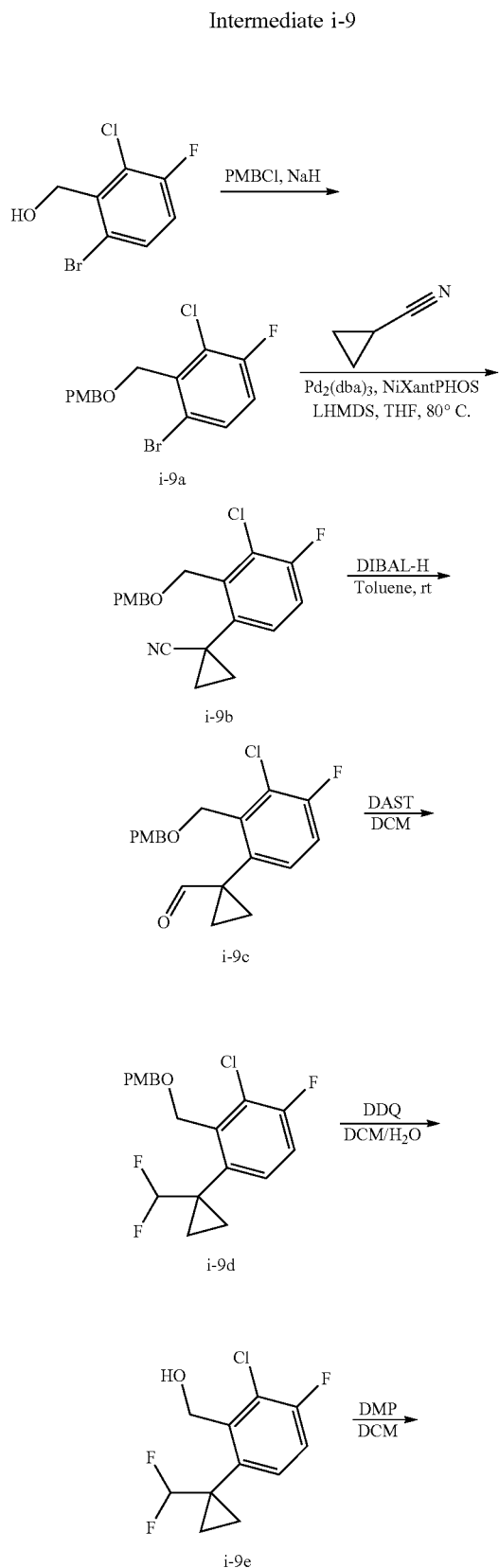

4-(1-(2-chloro-6-(1-(difluoromethyl)cyclopropyl)-3-fluorobenzoyl)-1H-pyrazolo[4,3-b]pyridin-3-yl)-3-fluorobenzoic acid (i-9)

Step 1: Preparation of 1-bromo-3-chloro-4-fluoro-2-(((4-methoxybenzyl)oxy) methyl) benzene To a solution of (6-bromo-2-chloro-3-fluorophenyl) methanol (3.5 g, 14.6 mmol) in DMF (40 mL) at 0° C. was added NaH (0.95 g, 23.75 mmol, 60% in mineral oil) and the reaction mixture was stirred at 0° C. for 30 min. Then 1-(chloromethyl)-4-methoxybenzene (2.75 g, 17.5 mmol) was added. The mixture was warmed to room temperature and stirred for 18 h. The mixture was quenched with water and extracted with EtOAc. The combined organics were washed with brine, dried over Na$_2$SO$_4$, filtered and concentrated. The residue was purified by silica gel column flash chromatography (0-5% EtOAc/hexanes) to give the title compound as a solid. $^1$H NMR (400 MHz, CDCl$_3$) δ 7.48 (dd, J=8.8 Hz, 5.1 Hz, 1H), 7.34 (d, J=8.4 Hz, 2H), 7.02 (t, J=8.5 Hz, 1H), 6.89 (d, J=8.4 Hz, 2H), 4.73-4.85 (m, 1H), 4.58 (s, 1H), 3.74-3.90 (m, 1H).

Step 2: Preparation of 1-(3-chloro-4-fluoro-2-(((4-methoxybenzyl)oxy)methyl)phenyl) cyclo propan-ecarbonitrile (i-9b)

4,6-Bis(diphenylphosphino)-10H-phenoxazine (0.48 g, 0.87 mmol) and Pd$_2$(dba)$_3$ (0.363 g, 0.396 mmol) were added to a flask containing THF (30 mL). The mixture was stirred at room temperature for 10 min under N$_2$. 1-bromo-3-chloro-4-fluoro methoxybenzyl)oxy)methyl)benzene i-9a (2.85 g, 7.93 mmol) and cyclopropanecarbonitrile (0.74 g, 11.0 mmol) were then added, followed by the immediate addition of lithium bis(trimethylsilyl)amide (13 mL, 13.00 mmol). The mixture was stirred at 80° C. for 18 h under N$_2$. The mixture was cooled to room temperature, diluted with aq. NH$_4$Cl and extracted with EtOAc. The combined organics were washed with brine, dried over Na$_2$SO$_4$, filtered and concentrated. The residue was purified by silica gel flash chromatography (0-20% EtOAc/hexanes) to give the title compound as an oil. $^1$H NMR (400 MHz, CDCl$_3$) δ 7.46 (d, J=7.5 Hz, 2H), 7.29-7.33 (m, 1H), 7.10 (t, J=8.5 Hz, 1H), 6.92 (d, J=8.4 Hz, 2H), 4.81-4.91 (m, 2H), 4.60-4.71 (m, 2H), 3.83 (s, 3H), 1.57-1.64 (m, 2H), 1.37-1.46 (m, 2H).

Step 3: Preparation of 1-(3-chloro-4-fluoro-2-(((4-methoxybenzyl)oxy)methyl) phenyl)cyclopropan-ecarbaldehyde (i-9c)

To a solution of 1-(3-chloro-4-fluoro-2-(((4-methoxybenzyl)oxy) methyl)phenyl)cyclopropanecarbonitrile i-9b (1.20 g, 3.47 mmol) in toluene (15 mL) was added DIBAL-H (7.3 mL, 7.3 mmol) at room temperature and the mixture was stirred at room temperature for 2 h. The mixture was cooled to 0° C., i-PrOH (8 mL) was added. After stirring at 0° C. for 30 min, 2M HCl (2 mL) was added to the reaction mixture. The resultant mixture was diluted with EtOAc (20 mL), filtered and rinsed with EtOAc. The filtrate was concentrated, and the residue was purified by silica gel flash chromatography (0-20% EtOAc/hexanes) to give the title compound as an oil. $^1$H NMR (400 MHz, CDCl$_3$) δ 9.08 (s, 1H), 7.30 (d, J=8.8 Hz, 2H), 7.15-7.18 (m, 1H), 7.07-7.13 (m, 1H), 6.90 (d, J=8.6 Hz, 2H), 4.59 (s, 2H), 4.52 (s, 2H), 3.82 (s, 3H), 1.57-1.59 (m, 2H), 1.39-1.46 (m, 2H).

Step 4: Preparation of 2-chloro-4-(1-(difluoromethyl)cyclopropyl)-1-fluoro-3-(((4-methoxy benzyl)oxy)methyl)benzene (i-9d)

To a mixture of 1-(3-chloro-4-fluoro-2-(((4-methoxybenzyl) oxy)methyl)phenyl)cyclopropanecarbaldehyde i-9c (650 mg, 1.864 mmol) in DCM (10 mL) was added DAST (0.8 mL, 6.1 mmol) at room temperature and the mixture was stirred at room temperature for 18 h. The mixture was concentrated, and the residue was purified by flash chromatography (0-10% EtOAc/hexanes) to give the title compound as an oil. $^1$H NMR (400 MHz, CDCl$_3$) δ 7.28-7.41 (m, 3H), 7.09 (t, J=8.5 Hz, 1H), 6.91 (d, J=7.9 Hz, 2H), 5.51-5.81 (m, 1H), 4.76 (brs, 2H), 4.61 (brs, 2H), 3.82 (s, 3H), 1.16 (brs, 2H), 1.03 (brs, 2H).

Step 5: Preparation of (2-chloro-6-(1-(difluoromethyl)cyclopropyl)-3-fluorophenyl) methanol DDQ (294 mg, 1.30 mmol) was added to a mixture of 2-chloro-4-(1-(difluoromethyl)cyclopropyl)-1-fluoro-3-(((4-methoxybenzyl)oxy)methyl)benzene i-9d (240 mg, 0.647 mmol) in DCM (3 mL) and water (0.5 mL) at room temperature. The mixture was stirred at room temperature for 1 h, quenched with aq. Na$_2$SO$_3$ (saturated, 20 mL) and extracted with DCM. The combined organics were washed with brine, dried over Na$_2$SO$_4$, filtered and concentrated. The residue was purified by silica gel flash chromatography (0-20% EtOAc/hexanes) to give the title compound as a gum. $^1$H NMR (400 MHz, CDCl$_3$) δ 7.34 (dd, J=8.4 Hz, 5.3 Hz, 1H), 7.11 (t, J=8.4 Hz, 1H), 5.45-5.79 (m, 1H), 5.01 (brs, 2H), 2.05-2.23 (m, 1H), 1.25-1.36 (m, 2H), 1.01-1.17 (m, 2H).

Step 6: Preparation of 2-chloro-6-(1-(difluoromethyl)cyclopropyl)-3-fluoro benz aldehyde (i-9f)

DMP (508 mg, 1.197 mmol) was added to a solution of (2-chloro-6-(1-(difluoromethyl)cyclopropyl)-3-fluorophenyl)methanol i-9e (150 mg, 0.60 mmol) in DCM (4 mL) at 0° C. and the mixture was stirred at room temperature for 3 h. The mixture was diluted with DCM, filtered, and rinsed with DCM (20 mL). The filtrate was concentrated, and the residue was purified by silica gel flash chromatography (0-10% EtOAc/hexanes) to give the title compound as a solid. $^1$H NMR (400 MHz, CDCl$_3$) δ 10.58 (s, 1H), 7.48 (dd, J=8.4 Hz, 5.1 Hz, 1H), 7.32 (t, J=8.4 Hz, 1H), 5.83-6.22 (m, 1H), 1.32-1.40 (m, 2H), 0.80 (brs, 2H).

Step 7: Preparation of 2-chloro-6-(1-(difluoromethyl)cyclopropyl)-3-fluorobenzoic acid (i-9)

2-Methylbut-2-ene (367 mg, 5.23 mmol) was added to a solution of 2-chloro-6-(1-(difluoromethyl)cyclopropyl)-3-fluorobenzaldehyde i-9f (130 mg, 0.52 mmol) in tert-butanol (4 mL) at room temperature. Then a solution of sodium dihydrogenphosphate (113 mg, 0.94 mmol) in water (1 mL) and sodium chlorite (60 mg, 0.66 mmol) in water (1 mL) was added respectively. The mixture was stirred at room temperature for 18 h. The mixture was quenched with 2M HCl (1 mL) and extracted with EtOAc. The combined organics were washed with brine, dried over Na$_2$SO$_4$, filtered and concentrated to give the title compound as a solid. $^1$H NMR (400 MHz, CDCl$_3$) δ 7.43 (dd, J=8.5 Hz, 4.8 Hz, 1H), 7.22 (t, J=8.5 Hz, 1H), 5.92-6.22 (m, 1H), 1.27-1.30 (m, 2H), 0.97-1.02 (m, 2H).

Intermediate i-10

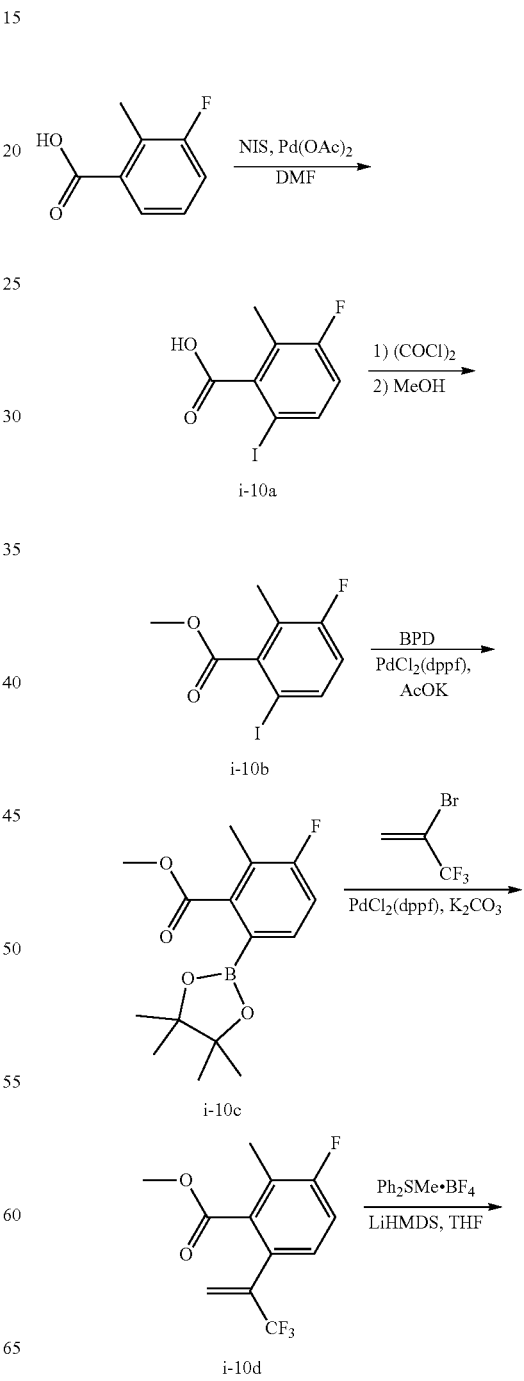

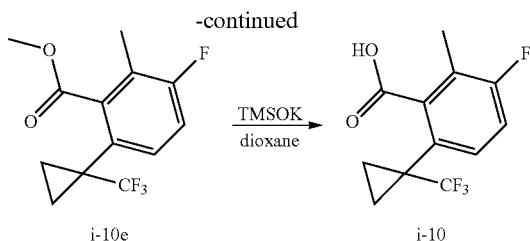

3-fluoro-4-(1-(3-fluoro-2-methyl-6-(1-(trifluoromethyl)cyclopropyl)benzoyl)-1H-pyrazolo[4,3-b]pyridin-3-yl)benzoic acid (i-10)

Step 1: Preparation of 3-fluoro-6-iodo-2-methylbenzoic acid (i-10a)

To a solution of 3-fluoro-2-methylbenzoic acid (3 g, 19.5 mmol) in DMF (30 mL) were added NIS (4.82 g, 21.4 mmol) and Pd(OAc)$_2$ (437 mg, 1.95 mmol). The mixture was stirred at 100° C. for 2 h. The reaction mixture was concentrated and the residue was purified by flash chromatography (1:1 EtOAc/hexanes) to give the title compound as a solid. $^1$H NMR (400 MHz, CDCl$_3$) δ 7.65 (dd, J=8.6 Hz, 4.8 Hz, 1H), 6.87 (t, J=8.8 Hz, 1H), 2.36 (d, J=1.8 Hz, 3H).

Step 2: Preparation of methyl 3-fluoro-6-iodo-2-methylbenzoate (i-10b)

To a solution of 3-fluoro-6-iodo-2-methylbenzoic acid i-10a (3.7 g, 13.2 mmol) in DCM (30 mL) were added oxalyl dichloride (5.0 g, 39.6 mmol) and DMF (48 mg, 0.66 mmol). The mixture was stirred at room temperature for 0.5 h, then concentrated. The residue was dissolved in methanol (40 mL) and the mixture was stirred at room temperature for 18 h. The mixture was concentrated and the residue was purified by flash chromatography (1:20 EtOAc/hexanes) to give the title compound as a solid. $^1$H NMR (400 MHz, CDCl$_3$) δ 7.60 (dd, J=8.2 Hz, 5.1 Hz, 1H), 6.82 (t, J=8.8 Hz, 1H), 3.96 (s, 3H), 2.24 (s, 3H).

Step 3: Preparation of methyl 3-fluoro-2-methyl-6-(4,4,5,5-tetramethyl-1,3,2-dioxaborolan-2-yl) benzoate (i-10c)

To a solution of methyl 3-fluoro-6-iodo-2-methylbenzoate i-10b (0.5 g, 1.7 mmol) in dioxane (5 mL) were added 4,4,4',4',5,5,5',5'-octamethyl-2,2'-bi (1,3,2-dioxaborolane) (0.77 g, 3.1 mmol), potassium acetate (217 mg, 2.21 mmol) and PdCl$_2$(dppf) (62 mg, 85 umol). The mixture was stirred at 100° C. for 18 h under N$_2$. The mixture was filtered and the filtrate was concentrated. The residue was purified by silica gel flash chromatography (1:100-1:20 EtOAc/hexanes) to give the title compound as a solid. $^1$H NMR (400 MHz, CDCl$_3$) δ 7.54-7.62 (m, 1H), 7.06 (t, J=8.8 Hz, 1H), 3.89 (s, 3H), 2.26 (d, J=1.5 Hz, 3H), 1.32 (s, 12H).

Step 4: Preparation of methyl 3-fluoro-2-methyl-6-(3,3,3-trifluoroprop-1-en-2-yl)benzoate (i-10d)

To a solution of methyl 3-fluoro-2-methyl-6-(4,4,5,5-tetramethyl-1,3,2-dioxaborolan-2-yl)benzoate i-10c (680 mg, 2.31 mmol), 2-bromo-3,3,3-trifluoroprop-1-ene (2.02 g, 11.6 mmol) in water (1 mL) and dioxane (7 mL) were added potassium carbonate (639 mg, 4.62 mmol) and PdCl$_2$(dppf) (84 mg, 116 umol). The mixture was stirred at 100° C. for 18 h under N$_2$. The mixture was concentrated and the residue was purified by silica gel flash chromatography (1:100-1:20 EtOAc/hexanes) to give the title compound (210 mg) as an oil. $^1$H NMR (400 MHz, CDCl$_3$) δ 7.15-7.22 (m, 1H), 7.06-7.13 (m, 1H), 6.02 (s, 1H), 5.56 (s, 1H), 3.83 (s, 3H), 2.27 (d, J=1.98 Hz, 3H).

Step 5: Preparation of methyl 3-fluoro-2-methyl-6-(1-(trifluoromethyl)cyclopropyl) benzoate (i-10e)

Methyl 3-fluoro-2-methyl-6-(3,3,3-trifluoroprop-1-en-2-yl)benzoate i-10d (0.5 g, 1.9 mmol) and methyldiphenylsulfonium tetrafluoroborate (1.10 g, 3.81 mmol) were dissolved in THF (5 mL), and the mixture was cooled to −78° C. Lithium bis(trimethylsilyl)amide (7.63 mL, 7.63 mmol) was added dropwise and the temperature was kept below −60° C. during addition. The mixture was stirred at −78° C. for 1 h, and then warmed to room temperature and stirred for 18 h. The reaction mixture was quenched with aq. NH$_4$Cl, and extracted with EtOAc. The combined organics were washed with brine, dried over Na$_2$SO$_4$, filtered and concentrated. The residue was purified by flash chromatography (0-5% EtOAc/hexanes) to give the title compound as an oil. $^1$H NMR (400 MHz, CDCl$_3$) δ 7.35 (dd, J=8.5 Hz, 5.2 Hz, 1H), 7.01-7.10 (m, 1H), 3.88-3.97 (m, 3H), 2.21 (d, J=2.2 Hz, 3H), 1.30-1.38 (m, 2H), 1.10 (brs, 2H).

Step 6: Preparation of 3-fluoro-2-methyl-6-(1-(trifluoromethyl)cyclopropyl)benzoic acid (i-10)

Potassium trimethylsilanolate (195 mg, 1.52 mmol) was added to a solution of methyl 3-fluoro-2-methyl-6-(1-(trifluoromethyl)cyclopropyl)benzoate i-10e (140 mg, 0.51 mmol) in dioxane (1.5 mL). The mixture was stirred at 90° C. for 18 h. The mixture was cooled, diluted with water, and extracted with EtOAc. The aqueous layer was collected, acidified with 2M HCl, and extracted with EtOAc. The combined organics were washed with brine, dried over Na$_2$SO$_4$, filtered and concentrated to give the title compound as a solid. $^1$H NMR (400 MHz, CDCl$_3$) δ 7.38 (dd, J=8.2 Hz, 5.3 Hz, 1H), 7.03-7.15 (m, 1H), 2.32 (d, J=1.8 Hz, 3H), 1.35-1.43 (m, 2H), 1.18 (brs, 2H).

Example 1A

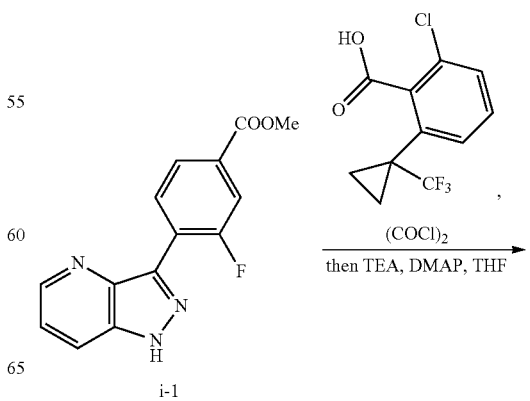

-continued

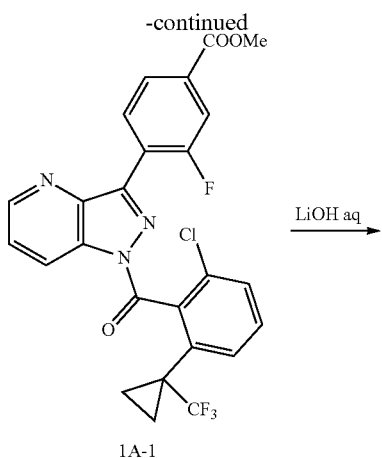

1A-1

↓ LiOH aq

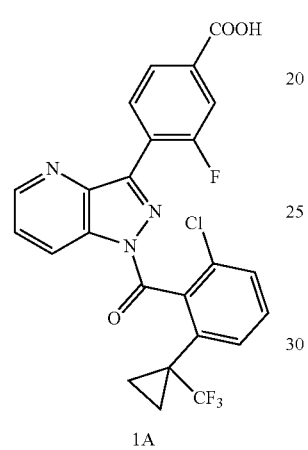

1A 4-(1-(2-chloro-6-(1-(trifluoromethyl)cyclopropyl)
benzoyl)-1H-pyrazolo[4,3-b]pyridin-3-yl)-3-fluo-
robenzoic acid (1A)

Step 1: Preparation of methyl 4-(1-(2-chloro-6-(1-
(trifluoromethyl)cyclopropyl) benzoyl)-1H-pyrazolo
[4,3-b]pyridin-3-yl)-3-fluorobenzoate (1A-1)

To a solution of 2-chloro-6-(1-(trifluoromethyl)cyclopropyl)benzoic acid i-3 (20 g, 76 mmol) in DCM (30 mL) at 0° C. were added DMF (0.28g, 3.8 mmol), followed by dropwise addition of oxalyl chloride (19 g, 151 mmol). After addition, the reaction mixture was stirred at room temperature for 2 h, and concentrated. The resulting crude acid chloride was dissolved in THF (210 mL), followed by the addition of methyl 3-fluoro-4-(1H-pyrazolo[4,3-b]pyridin-3-yl)benzoate i-1 (HCl salt, 21g, 68 mmol), DMAP (16.7g, 136 mmol), and TEA (20.7g, 205 mmol) at 0° C. After addition, cooling bath was removed and the reaction mixture was stirred at 80° C. for 12 h. The reaction mixture was cooled down, diluted with H₂O, and extracted with DCM. The organic layer was separated, washed with brine, dried over Na₂SO₄, and concentrated. The crude residue was purified by flash chromatography (0-50% hexanes/EtOAc) to afford the desired product. ¹H NMR (400 MHz, CDCl₃) δ 8.92-8.99 (m, 1H), 8.83-8.91 (m, 1H), 8.23 (t, J=7.4 Hz, 1H), 7.90-7.99 (m, 1H), 7.82 (d, J=10.6 Hz, 1H), 7.55-7.66 (m, 2H), 7.43-7.51 (m, 2H), 3.94 (s, 3H), 1.33-1.44 (m, 1H), 1.17-1.31 (m, 2H), 0.83-0.96 (m, 1H).

Step 2: Preparation of 4-(1-(2-chloro-6-(1-(trifluoromethyl)cyclopropyl)benzoyl)-1H-pyrazolo [4,3-b]
pyridin-3-yl)-3-fluorobenzoic acid (1A)

To a solution of methyl 4-(1-(2-chloro-6-(1-(trifluoromethyl) cyclopropyl)benzoyl)-1H-pyrazolo[4,3-b]pyridin-3-yl)-3-fluorobenzoate 1A-1 (32.9g, 64 mmol) in THF (300 mL) was added 1M LiOH (142 ml, 142 mmol). The reaction mixture was stirred at room temperature for 2 h, and LCMS showed complete conversion. Then 1M HCl (100 ml, 100 mmol) was added dropwise. Then 500 mg of the final product (from front run) was added as seeds, followed by the addition of additional 1N HCl (42 ml, 42 mmol). Then 350 ml of H₂O was added. The resulting suspension was stirred at rt for 30 min. The desired final product was obtained as white solid filtration, and drying under vacuum. ¹H NMR (400 MHz, CDCl₃) δ 8.98 (d, J=8.6 Hz, 1H), 8.88 (dd, J=3.7 Hz, 1.0 Hz, 1H), 8.16 (t, J=7.4 Hz, 1H), 7.91-7.99 (m, 1H), 7.83 (d, J=10.2 Hz, 1H), 7.55-7.70 (m, 2H), 7.43-7.52 (m, 2H), 1.18-1.43 (m, 4H), 0.92 (s, 1H). LCMS: 504 (M+1).

Example 1B

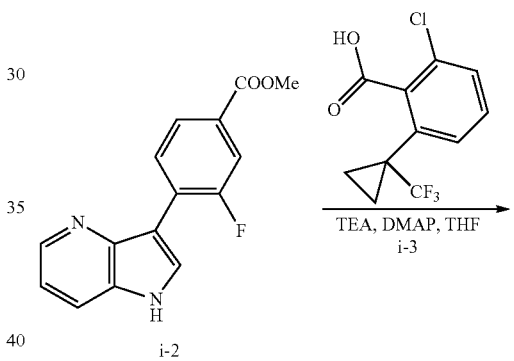

↓ TEA, DMAP, THF

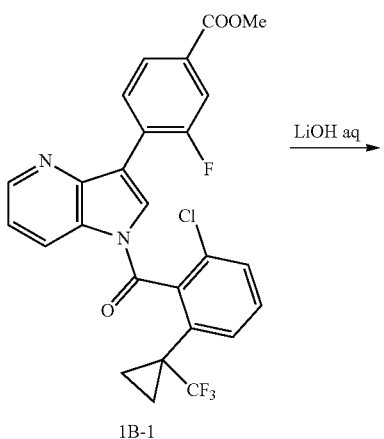

1B-1

↓ LiOH aq

-continued

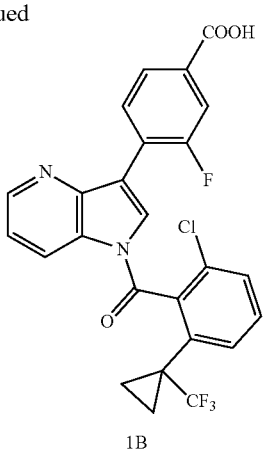

1B 4-(1-(2-chloro-6-(1-(trifluoromethyl)cyclopropyl)
benzoyl)-1H-pyrrolo[3,2-b]pyridin-3-yl)-3-fluo-
robenzoic acid (1B)

Step 1: Preparation of methyl 4-(1-(2-chloro-6-(1-
(trifluoromethyl)cyclopropyl) benzoyl)-1H-pyrrolo
[3,2-b]pyridin-3-yl)-3-fluorobenzoate (1B-1)

To a solution of methyl 3-fluoro-4-(1H-pyrrolo[3,2-b] pyridin-3-yl) benzoate i-2 (60 mg, 0.222 mmol) in THF (1.0 mL) at room temperature was added NaH (27 mg, 0.67 mmol, 60% ub mineral oil). The mixture was stirred for 20 min, followed by the addition of 2-chloro-6-(1-(trifluoromethyl)cyclopropyl)benzoyl chloride (~0.55 mmol, dissolved in 1.0 mL THF) (prepared by following the same procedure described in the synthesis of example 1A). The reaction mixture was stirred at room temperature for 20 min, diluted with sat NH$_4$Cl, and extracted with EtOAc. The combined organics were washed with brine, dried over MgSO$_4$, and concentrated. The crude residue was used in the next step without further purification. LCMS: 517 (M+1).

Step 2: Preparation of 4-(1-(2-chloro-6-(1-(trifluo-
romethyl)cyclopropyl)benzoyl)-1H-pyrrolo[3,2-b]
pyridin-3-yl)-3-fluorobenzoic acid (1B)

To a solution of methyl 4-(1-(2-chloro-6-(1-(trifluorom-ethyl)cyclopropyl)benzoyl)-1H-pyrrolo[3,2-b]pyridin-3-yl)-3-fluorobenzoate 1B-1 (crude aliquot from previous step, 30 mg, 0.058 mmol) in THF (1.0 mL)/MeOH (1.0 mL) at room temperature was added 2M LiOH (0.29 ml, 0.58 mmol). The mixture was stirred at room temperature for 3 h. The mixture was acidified with 2N HCl, extracted with EtOAc. The organics were concentrated. The residue was purified by reversed-phase HPLC(H$_2$O/CH$_3$CN containing 0.1% TFA) to give the final product as a solid. $^1$H NMR (DMSO-d6, 600 MHz) δ 13.29 (brs, 1H), 8.73-8.88 (m, 2H), 7.57-7.89 (m, 5H), 1.24-1.42 (m, 3H), 0.92-1.00 (m, 1H). MS: 503 (M+1).

The following examples shown in Table 1 were prepared following similar procedures described for the synthesis of 1A or 1B, and can be achieved by those of ordinary skill in the art of organic synthesis.

TABLE 1

| Example No. | Structure | IUPAC Name | Exact Mass [M + H]+ | $^1$H-NMR |
|---|---|---|---|---|
| 1C | ![structure] | 3-fluoro-4-(1-(2-methyl-6-(1-(trifluoromethyl)cyclopropyl)benzoyl)-1H-pyrazolo[4,3-b]pyridin-3-yl)benzoic acid | 484 | $^1$H NMR (400 MHz, CDCl$_3$) δ 9.02 (d, J = 8.2 Hz, 1H), 8.87 (d, J = 3.9 Hz, 1H), 8.11 (t, J = 7.4 Hz, 1H), 7.93 (d, J = 8.2 Hz, 1H), 7.82 (d, J = 10.2 Hz, 1H), 7.63-7.66 (m, 1H), 7.46-7.50 (m, 1H), 7.39-7.44 (m, 1H), 7.28 (d, J = 7.4 Hz, 1H), 2.19 (s, 3H), 1.30-1.36 (m, 1H), 1.25 (brs, 1H), 1.14-1.21 (m, 1H), 0.84 (brs, 1H). |

TABLE 1-continued

| Example No. | Structure | IUPAC Name | Exact Mass [M + H]+ | ¹H-NMR |
|---|---|---|---|---|
| 1D | 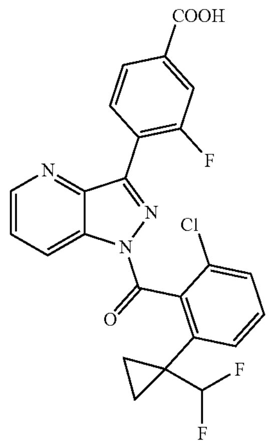 [SMILES: O=C(O)c1ccc(-c2nn(C(=O)c3c(Cl)cccc3C3(C(F)F)CC3)c3cccnc23)c(F)c1] | 4-(1-(2-chloro-6-(1-(difluoromethyl)cyclopropyl)benzoyl)-1H-pyrazolo[4,3-b]pyridin-3-yl)-3-fluorobenzoic acid | 486 | ¹H NMR (400 MHz, CDCl₃) δ 8.93 (d, J = 8.6 Hz, 1H), 8.87 (d, J = 4.3 Hz, 1H), 8.21 (t, J = 7.4 Hz, 1H), 7.95 (d, J = 8.2 Hz, 1H), 7.84 (d, J = 11.0 Hz, 1H), 7.63 (dd, J = 8.6 Hz, 4.7 Hz, 1H), 7.48-7.53 (m, 1H), 7.39-7.47 (m, 2H), 6.05-6.34 (m, 1H), 1.24-1.33 (m, 1H), 1.03 (brs, 1H), 0.90 (brs, 1H), 0.60 (brs, 1H). |
| 1E | 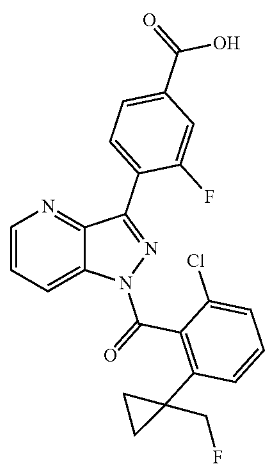 [SMILES: O=C(O)c1ccc(-c2nn(C(=O)c3c(Cl)cccc3C3(CF)CC3)c3cccnc23)c(F)c1] | 4-(1-(2-chloro-6-(1-(fluoromethyl)cyclopropyl)benzoyl)-1H-pyrazolo[4,3-b]pyridin-3-yl)-3-fluorobenzoic acid | 468 | ¹H NMR (400 MHz, CDCl₃) δ 8.98 (d, J = 8.2 Hz, 1H), 8.89 (d, J = 3.9 Hz, 1H), 8.17 (t, J = 7.2 Hz, 1H), 7.96 (d, J = 7.8 Hz, 1H), 7.85 (d, J = 10.2 Hz, 1H), 7.67 (dd, J = 8.2 Hz, 4.3 Hz, 1H), 7.51 (d, J = 6.6 Hz, 1H), 7.36-7.47 (m, 2H), 4.68-4.89 (m, 1H), 3.96-4.16 (m, 1H), 0.95-1.15 (m, 2H), 0.68 (t, J = 6.6 Hz, 2H). |
| 1F | 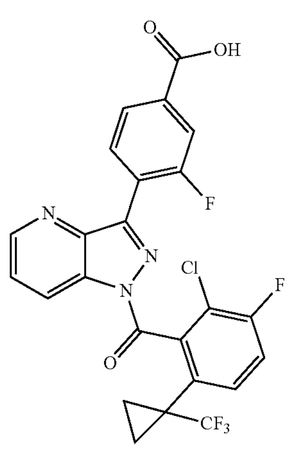 [SMILES: O=C(O)c1ccc(-c2nn(C(=O)c3c(C4(C(F)(F)F)CC4)ccc(F)c3Cl)c3cccnc23)c(F)c1] | 4-(1-(2-chloro-3-fluoro-6-(1-(trifluoromethyl)cyclopropyl)benzoyl)-1H-pyrazolo[4,3-b]pyridin-3-yl)-3-fluorobenzoic acid | 522 | ¹H NMR (400 MHz, CDCl₃) δ 8.95 (d, J = 8.4 Hz, 1H), 8.87 (d, J = 3.5 Hz, 1H), 8.17 (t, J = 7.3 Hz, 1H), 7.96 (d, J = 8.0 Hz, 1H), 7.84 (d, J = 9.9 Hz, 1H), 7.65 (dd, J = 8.4 Hz, 4.5 Hz, 1H), 7.56 (dd, J = 8.5 Hz, 4.6 Hz, 1H), 7.31 (t, J = 8.4 Hz, 1H), 1.33-1.40 (m, 1H), 1.18-1.30 (m, 2H), 0.88 (brs, 1H). |

TABLE 1-continued

| Example No. | Structure | IUPAC Name | Exact Mass [M + H]+ | ¹H-NMR |
|---|---|---|---|---|
| 1G | 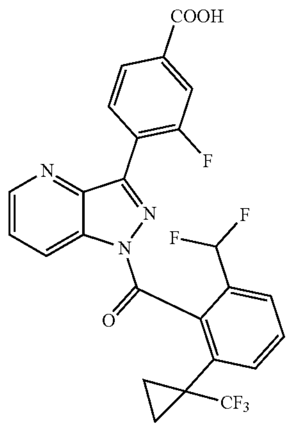 [SMILES: O=C(O)c1ccc(-c2nn(C(=O)c3c(C(F)F)cccc3C3(C(F)(F)F)CC3)c3cccnc23)c(F)c1] | 4-(1-(2-(difluoromethyl)-6-(1-(trifluoromethyl)cyclopropyl)benzoyl)-1H-pyrazolo[4,3-b]pyridin-3-yl)-3-fluorobenzoic acid | 520 | ¹H NMR (400 MHz, CDCl₃) δ 8.99 (d, J = 8.4 Hz, 1H), 8.87 (d, J = 4.0 Hz, 1H), 8.20-8.32 (m, 1H), 7.96 (d, J = 8.2 Hz, 1H), 7.68-7.90 (m, 5H), 6.57-6.91 (m, 1H), 1.18-1.46 (m, 3H), 0.91 (brs, 1H). |
| 1H | 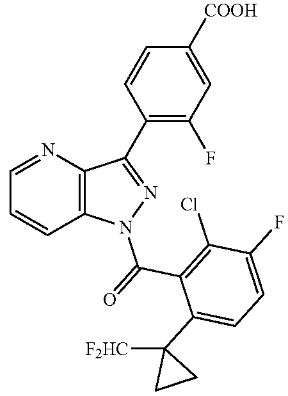 [SMILES: O=C(O)c1ccc(-c2nn(C(=O)c3c(C4(C(F)F)CC4)ccc(F)c3Cl)c3cccnc23)c(F)c1] | 4-(1-(2-chloro-6-(1-(difluoromethyl)cyclopropyl)-3-fluorobenzoyl)-1H-pyrazolo[4,3-b]pyridin-3-yl)-3-fluorobenzoic acid | 504 | ¹H NMR (400 MHz, CDCl₃) δ 8.82-9.03 (m, 2H), 8.23 (t, J = 7.4 Hz, 1H), 7.99 (d, J = 7.7 Hz, 1H), 7.87 (d, J = 10.1 Hz, 1H), 7.69 (dd, J = 8.3 Hz, 4.5 Hz, 1H), 7.51 (dd, J = 8.6 Hz, 4.6 Hz, 1H), 7.31 (t, J = 8.6 Hz, 1H), 6.00-6.33 (m, 1H), 1.25-1.37 (m, 1H), 1.04 (brs, 1H), 0.93 (brs, 1H), 0.61 (brs, 1H). |

TABLE 1-continued

| Example No. | Structure | IUPAC Name | Exact Mass [M + H]+ | $^1$H-NMR |
|---|---|---|---|---|
| 1I | (structure) | 3-fluoro-4-(1-(3-fluoro-2-methyl-6-(1-(trifluoromethyl)cyclopropyl)benzoyl)-1H-pyrazolo[4,3-b]pyridin-3-yl)benzoic acid | 502 | $^1$H NMR (400 MHz, CDCl$_3$) δ 9.01 (d, J = 8.4 Hz, 1H), 8.89 (d, J = 4.2 Hz, 1H), 8.11-8.19 (m, 1H), 7.97 (d, J = 7.9 Hz, 1H), 7.85 (d, J = 10.4 Hz, 1H), 7.67 (dd, J = 8.5 Hz, 4.5 Hz, 1H), 7.44-7.50 (m, 1H), 7.19 (t, J = 8.8 Hz, 1H), 2.10 (s, 3H), 1.13-1.37 (m, 3H), 0.82 (brs, 1H). |
| 1J | (structure) | 4-(1-(2-chloro-6-(1-(trifluoromethyl)cyclopropyl)benzoyl)-1H-pyrrolo[3,2-b]pyridin-3-yl)-3-fluorobenzoic acid | 485 | $^1$H NMR (600 MHz, DMSO-d6) δ 13.28 (s, 1H), 8.80-8.87 (m, 2H), 8.73 (d, J = 4.8 Hz, 1H), 7.56-7.92 (m, 6H), 5.84 (t, J = 57 Hz, 1H), 1.14-1.22 (m, 2H), 0.93-0.98 (m, 1H), and 0.70-0.76 (m, 1H). |

Experimental Procedure for Collecting Rat PK:

Pharmacokinetic parameters were determined following PO and IV dosing at 1 mg/kg and 0.5 mg/kg or 0.05 mg/kg respectively in fasted male Wistar Han rats. Compounds were formulated for both PO and IV dosing in 20/60/20 DMSO/PEG400/H$_2$O. Plasma samples obtained from dosed animals were acidified by adding 30 μL of 2% formic acid to 100 μL of plasma to stabilize potential acyl-glucuronide metabolites. Sample clean-up was carried out by means of a single step protein precipitation technique by adding 200 μL of acetonitrile to 50 μL aliquots of individual subject samples. Samples were mixed by vortex for homogeneity and then subjected to centrifugation at 3500 rpm for 10 min. The supernatant (200 μL) was collected and an aliquot was injected into the LC-MS/MS for analysis. Pharmacokinetic parameters were calculated using established non-compartmental methods. The area under the plasma concentration versus time curve (AUC) was determined using the Watson software (version 7.3) or Phoenix Professional (version 6.2.1), with linear trapezoidal interpolation in the ascending slope and logarithmic trapezoidal interpolation in the descending slope. The portion of the AUC from the last measurable concentration to infinity was estimated from the equation, Ct/kel, where Ct represents the last measurable concentration and kel is the elimination rate constant. The latter was determined from the concentration versus time curve by linear regression at the terminal phase of the semi-logarithmic plot.

TABLE 2

Clearance comparison with historical compound

| Example No. | Rat plasma clearance (Clp) ml/min/kg |
|---|---|
| 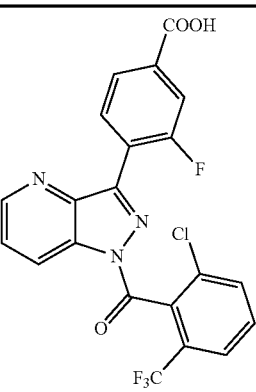 Disclosed in U.S. Pat. No. 9,095,583 | 76 |
| 1A | 6 |
| 1B | 5 |

TABLE 2-continued

Clearance comparison with historical compound

| Example No. | Rat plasma clearance (Clp) ml/min/kg |
|---|---|
| 1C | 21 |
| 1D | 10 |
| 1E | 16 |
| 1F | 8 |
| 1G | 5 |
| 1H | 16 |
| 1I | 18 |
| 1J | 5 |

Biological Assay

The compounds of the invention inhibit RORgammaT activity. Activation of RORgammaT activity can be measured using, e.g., biochemical TR-FRET assay. In such an assay, interaction of cofactor-derived peptides with human RORgammaT-Ligand Binding Domain (LBD) can be measured. The TR-FRET technique is a sensitive biochemical proximity assay that will give information concerning the interaction of a ligand with the LBD, in the presence of cofactor-derived peptides (Zhou et al., Methods 25:54-61, 2001).

To identify novel antagonists of RORgammaT, an assay was developed which employs the interaction of RORgammaT with its co-activator peptide SRC1_2. This peptide mimics the recruitment of co-activators to RORgammaT through its interaction with the LXXLL (e.g., NR box) motifs (Xie et al., J. Immunol. 175: 3800-09, 2005; Kurebayashi et al., Biochem. Biophys. Res. Commun. 315: 919-27, 2004; Jin et al., Mol. Endocrinology 24:923-29, 2010). The RORγ-Ligand Binding Domain TR-FRET Assay was run according to the following protocol.

HIS-tagged RORγ-LBD protein was recombinantly expressed in *Escherichia coli*. The RORγ-LBD protein was purified by Ni2+-affinity resin. Purified protein was then diluted in assay buffer (50 mM Tris pH 7.0, 50 mM KCl, 1 mM EDTA, 0.1 mM DTT, 100 mg/ml bovine serum albumin, delipidated) to obtain a RORγ-LBD final concentration of 3 nM. Europium tagged anti-HIS antibody was also added to this solution (1.25 nM). Separately, SF9 cells not expressing any recombinant protein were lysed (32,000 cells per ml in 25 mM Tris, 50 mM NaCl) and the previously frozen lysate was added to the diluted RORγ-LBD solution at a ratio of 0.75 ml SF9 lysate per 15 ml of diluted RORγ-LBD.

Compounds to be tested were injected to the 384-well assay plate using Acoustic Droplet Ejection technology by Echo 550 liquid handler (Labcyte, Calif.).

A stock of biotinylated-LXXLL peptide from coactivator SRC1 (Biotin-SPSSHSSLTERHKILHRLLQEGSP) (SEQ ID NO:1) and APC-conjugated streptavidin (final concentrations 100 nM and 8 nM respectively) were also added to each well.

The final assay mixture was incubated overnight at 4° C., warmed to room temperature and the fluorescence signal was measured on an Envision plate reader: (Excitation filter=340 nm; APC emission=665 nm; Europium emission=615 nm; dichroic mirror=D400/D630; delay time=100 μs, integration time=200 μs). IC50 values for test compounds were calculated from the quotient of the fluorescence signal at 665 nm divided by the fluorescence signal at 615 nm.

The IC$_{50}$ values for representative compounds of the invention are set forth below.

| Example No. | Fret IC$_{50}$ (nM) |
|---|---|
| 1A | 1.6 |
| 1B | 2.5 |
| 1C | 4.1 |
| 1D | 1.4 |
| 1E | 1.2 |
| 1F | 1.5 |
| 1G | 2.0 |
| 1H | 1.1 |
| 1I | 2.4 |
| 1J | 1.4 |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within.

What is claimed is:

1. A compound according to Formula I:

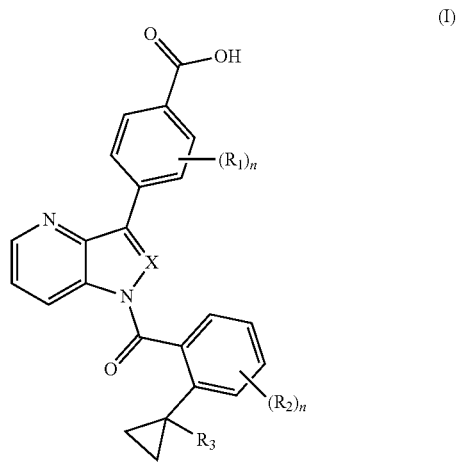

(I)

wherein:

X is CH or N;

n is 0, 1 or 2;

R$_1$ is independently OH, halo or (C$_{1-4}$)alkyl;

R$_2$ is independently OH, halo, (C$_{1-4}$)alkyl, CH$_2$F, CHF$_2$ or CF$_3$; and R$_3$ is CH$_2$F, CHF$_2$ or CF$_3$;

or a pharmaceutically acceptable salt thereof.

2. A compound according to claim 1, wherein the compound is represented by Formula

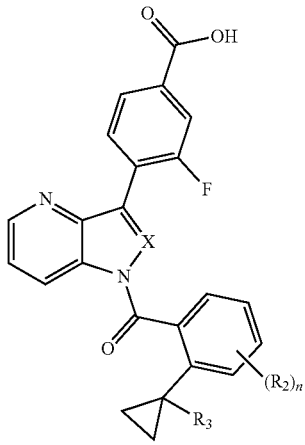

(II)

wherein:
X is CH or N;
n is 1 or 2;
$R_2$ is independently OH, halo, $(C_{1-4})$alkyl, $CH_2F$, $CHF_2$ or $CF_3$; and
$R_3$ is $CH_2F$, $CHF_2$ or $CF_3$;
or a pharmaceutically acceptable salt thereof.

3. A compound according to claim 1, wherein the compound is represented by Formula III:

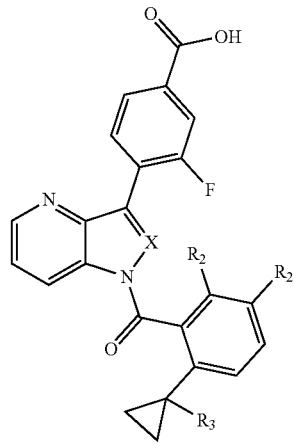

(III)

wherein:
X is CH or N;
$R_2$ is independently H, Cl, F, $CH_3$ or $CHF_2$; and
$R_3$ is $CH_2F$, $CHF_2$ or $CF_3$;
or a pharmaceutically acceptable salt thereof.

4. A compound according to claim 1, wherein $R_1$ is chloro or fluoro.

5. A compound according to claim 1, wherein $R_1$ is fluoro.

6. A compound according to claim 2, wherein n is 1.

7. A compound according to claim 6, wherein $R_2$ is chloro or fluoro.

8. A compound according to claim 6, wherein $R_2$ is chloro.

9. A compound according to claim 8, wherein X is N.

10. A compound according to claim 8, wherein X is CH.

11. A compound according to claim 9, wherein $R_3$ is $CF_3$.

12. A compound according to claim 11, wherein the compound is in the form of a free acid.

13. A compound selected from:

3-fluoro-4-(1-(2-methyl-6-(1-(trifluoromethyl)cyclopropyl)benzoyl)-1H-pyrazolo[4,3-b]pyridin-3-yl)benzoic acid;

4-(1-(2-chloro-6-(1-(difluoromethyl)cyclopropyl) benzoyl)-1H-pyrazolo[4,3-b]pyridin-3-yl)-3-fluorobenzoic acid;

4-(1-(2-chloro-6-(1-(trifluoromethyl)cyclopropyl)benzoyl)-1H-pyrazolo[4,3-b]pyridin-3-yl)-3-fluorobenzoic acid;

4-(1-(2-chloro-3-fluoro-6-(1-(trifluoromethyl)cyclopropyl)benzoyl)-1H-pyrazolo[4,3-b]pyridin-3-yl)-3-fluorobenzoic acid;

4-(1-(2-(difluoromethyl)-6-(1-(trifluoromethyl)cyclopropyl)benzoyl)-1H-pyrazolo[4,3-b]pyridin-3-yl)-3-fluorobenzoic acid;

4-(1-(2-chloro-6-(1-(difluoromethyl)cyclopropyl)-3-fluorobenzoyl)-1H-pyrazolo[4,3-b]pyridin-3-yl)-3-fluorobenzoic acid;

3-fluoro-4-(1-(3-fluoro-2-methyl-6-(1-(trifluoromethyl)cyclopropyl)benzoyl)-1H-pyrazolo[4,3-b]pyridin-3-yl) benzoic acid; and 4-(1-(2-chloro-6-(1-(trifluoromethyl)cyclopropyl)benzoyl)-1H-pyrrolo[3,2-b]pyridin-3-yl)-3-fluorobenzoic acid;

or a pharmaceutically acceptable salt thereof.

14. A pharmaceutical composition comprising a compound of claim 1 or a pharmaceutically acceptable salt thereof, and one or more pharmaceutically acceptable carriers.

15. A pharmaceutical composition comprising a compound of claim 13 or a pharmaceutically acceptable salt thereof, and one or more pharmaceutically acceptable carriers.

16. A method of treating a disorder selected from the group consisting of an autoimmune disorder and an inflammatory disorder, comprising administering to a subject in need thereof a therapeutically effective amount of a compound of claim 1 to treat the disorder.

17. The method of claim 16, wherein the disorder is an autoimmune disorder.

18. The method of claim 17, wherein the autoimmune disorder is rheumatoid arthritis, psoriasis, Crohn's disease, inflammatory bowel disease, multiple sclerosis, ankylosing spondylitis, systemic lupus erythematosus, chronic graft-versus-host disease, acute graft-versus-host disease, Celiac Sprue, idiopathic thrombocytopenic thrombotic purpura, myasthenia gravis, Sjogren's syndrome, scleroderma, ulcerative colitis, or epidermal hyperplasia.

19. The method of claim 16, wherein the disorder is an inflammatory disorder.

20. A method of inhibiting the activity of a RORγ, comprising exposing a RORγ to an effective amount of a compound of claim 1 to inhibit the activity of said RORγ.

21. The method of claim 18, wherein the compound is

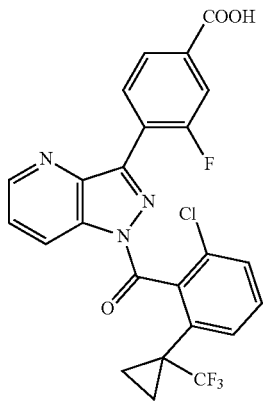 [SMILES: O=C(O)c1ccc(-c2nn(C(=O)c3c(Cl)cccc3C3(C(F)(F)F)CC3)c3cccnc23)c(F)c1]

or a pharmaceutically acceptable salt thereof.

22. A compound having the following formula:

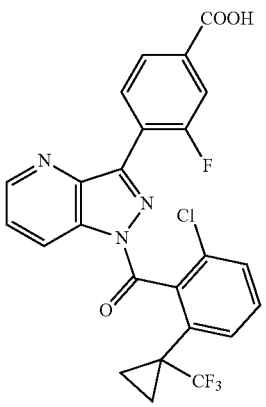 [SMILES: O=C(O)c1ccc(-c2nn(C(=O)c3c(Cl)cccc3C3(C(F)(F)F)CC3)c3cccnc23)c(F)c1]

or a pharmaceutically acceptable salt thereof.

23. A pharmaceutical composition comprising a compound of claim 22 and one or more pharmaceutically acceptable carriers.

* * * * *